(12) United States Patent
Sippy et al.

(10) Patent No.: US 12,090,159 B2
(45) Date of Patent: Sep. 17, 2024

(54) DEUTERATED FORMS OF TESTOSTERONE AND METHODS OF USE

(71) Applicant: Lennham Pharmaceuticals, Inc., Concord, MA (US)

(72) Inventors: Bradford C. Sippy, Acton, MA (US); Benjamin D. Enerson, Sudbury, MA (US)

(73) Assignee: Lennham Pharmaceuticals, Inc., Concord, MA (US)

( * ) Notice: Subject to any disclaimer, the term of this patent is extended or adjusted under 35 U.S.C. 154(b) by 124 days.

(21) Appl. No.: 17/966,245

(22) Filed: Oct. 14, 2022

(65) Prior Publication Data

US 2023/0124138 A1   Apr. 20, 2023

Related U.S. Application Data

(63) Continuation of application No. 17/556,859, filed on Dec. 20, 2021, now Pat. No. 11,471,469, which is a continuation of application No. 17/210,082, filed on Mar. 23, 2021, now Pat. No. 11,202,785.

(60) Provisional application No. 63/121,766, filed on Dec. 4, 2020.

(51) Int. Cl.
   *A61K 31/568*  (2006.01)
(52) U.S. Cl.
   CPC ................... *A61K 31/568* (2013.01)
(58) Field of Classification Search
   CPC .................................................. A61K 31/568
   See application file for complete search history.

(56) References Cited

U.S. PATENT DOCUMENTS

| | | | |
|---|---|---|---|
| 4,069,346 | A | 1/1978 | McCarty |
| 11,202,785 | B1 | 12/2021 | Sippy et al. |
| 11,471,469 | B2 | 10/2022 | Sippy et al. |
| 2002/0150625 | A1 | 10/2002 | Kryger |
| 2011/0251167 | A1 | 10/2011 | Dudley et al. |
| 2013/0011850 | A1 | 1/2013 | Zhang et al. |
| 2014/0161827 | A1 | 6/2014 | Santen et al. |
| 2024/0000799 | A1 | 1/2024 | Sippy et al. |

FOREIGN PATENT DOCUMENTS

WO   WO 2014/093818 A2   6/2014

OTHER PUBLICATIONS

U.S. Appl. No. 17/210,082, filed Mar. 23, 2021, Sippy et al.
U.S. Appl. No. 17/556,859, filed Dec. 20, 2021, Sippy et al.
PCT/US2021/061618, Feb. 14, 2022, Invitation to Pay Additional Fees.
PCT/US2021/061618, Apr. 12, 2022, International Search Report and Written Opinion.
Invitation to Pay Additional Fees for PCT/US2021/061618, mailed on Feb. 14, 2022.
International Search Report and Written Opinion for PCT/US2021/061618, mailed on Apr. 12, 2022.
Baba et al., Differentiation between endogenous and exogenous testosterone in human plasma and urine after oral administration of deuterium-labeled testosterone by mass fragmentography. J Clin Endocrinol Metab. May 1980;50(5):889-94. doi: 10.1210/jcem-50-5-889.
Baba et al., Synthesis of trideuterated testosterone labeled selectively at the C-19 angular methyl group. J Label Comp Radiopharma. 1978;14(5):783-791.
Boni et al., Therapeutic activity of testosterone in metastatic breast cancer. Anticancer Res. Mar. 2014;34(3):1287-90.
CAS No. 69660-28-2. 2019 BDG Synthesis.
Fujioka et al., Pharmacokinetic properties of testosterone propionate in normal men. J Clin Endocrinol Metab. Dec. 1986;63(6):1361-4. doi: 10.1210/jcem-63-6-1361.
Fujioka et al., Acute suppression of endogenous testosterone levels by exogenous testosterone in normal men. Life Sci. Aug. 24, 1987;41(8):945-9. doi: 10.1016/0024-3205(87)90681-3.
Gardner et al., Progress on the road to better medical care for transgender patients. Curr Opin Endocrinol Diabetes Obes. Dec. 2013;20(6):553-8. doi: 10.1097/01.med.0000436188.95351.4d.
Glaser et al., Subcutaneous testosterone-letrozole therapy before and concurrent with neoadjuvant breast chemotherapy: clinical response and therapeutic implications. Menopause. Jul. 2017;24(7):859-864. doi: 10.1097/GME.0000000000000828.
Hickey et al., The androgen receptor is a tumor suppressor in estrogen receptor-positive breast cancer. Nat Med. Feb. 2021;27(2):310-320. doi: 10.1038/s41591-020-01168-7. Epub Jan. 18, 2021.
Macedo et al., Role of androgens on MCF-7 breast cancer cell growth and on the inhibitory effect of letrozole. Cancer Res. Aug. 1, 2006;66(15):7775-82. doi: 10.1158/0008-5472.CAN-05-3984.
Ortmann et al., Testosterone and 5 alpha-dihydrotestosterone inhibit in vitro growth of human breast cancer cell lines. Gynecol Endocrinol. Apr. 2002;16(2):113-20.
Petering et al., Testosterone Therapy: Review of Clinical Applications. Am Fam Physician. Oct. 1, 2017;96(7):441-449. Erratum in: Am Fam Physician. Oct. 1, 2019;100(7):393.
Sanaullah et al., Facile synthesis of [16,16,17-2H3]-testosterone, -epitestosterone and their glucuronides and sulfates. J Steroid Biochem Mol Biol. May 1996;58(2):225-34. doi: 10.1016/0960-0760(96)00025-8. Abstract only.
Shinohara et al., Synthesis of deuterium labeled 17-methyl-testosterone. Steroids. Sep. 1984;44(3):253-60. doi: 10.1016/0039-128x(84)90006-0.

(Continued)

*Primary Examiner* — James D. Anderson
(74) *Attorney, Agent, or Firm* — Wolf, Greenfield & Sacks, P.C.

(57) ABSTRACT

Provided herein are compositions (e.g., pharmaceutical compositions) comprising deuterated testosterone, deuterated methyltestosterone, or derivatives thereof. The provided compositions and related methods may be useful for treating and/or preventing various diseases and conditions, such as hypogonadism, delay of growth and puberty, weight loss associated with HIV-associated wasting, vulvar dystrophies, micropenis, breast cancer, and sexual disorders.

20 Claims, 4 Drawing Sheets

(56) References Cited

OTHER PUBLICATIONS

Shoskes et al., Pharmacology of testosterone replacement therapy preparations. Transl Androl Urol. Dec. 2016;5(6):834-843. doi: 10.21037/tau.2016.07.10.
Sikora et al., The androgen metabolite 5alpha-androstane-3beta, 1 7beta-diol (3betaAdiol) induces breast cancer growth via estrogen receptor: implications for aromatase inhibitor resistance. Breast Cancer Res Treat. May 2009; 115(2):289-96. doi: 10.1007/s10549-008-0080-8. Epub Jun. 4, 2008.
Timmins, G.S. Deuterated drugs; updates and obviousness analysis. Expert Opin Ther Pat. Dec. 2017;27(12):1353-1361. doi: 10.1080/13543776.2017.1378350. Epub Sep. 14, 2017. Erratum in: Expert Opin Ther Pat. Aug. 2018;28(8):653.
Tsametis et al., Testosterone replacement therapy: For whom, when and how? Metabolism. Sep. 2018;86:69-78. doi: 10.1016/j.metabol. 2018.03.007. Epub Mar. 9, 2018.
Yu et al., Selective Androgen Receptor Modulator RAD140 Inhibits the Growth of Androgen/Estrogen Receptor-Positive Breast Cancer Models with a Distinct Mechanism of Action. Clin Cancer Res. Dec. 15, 2017;23(24):7608-7620. doi: 10.1158/1078-0432.CCR-17-0670. Epub Oct. 3, 2017.
International Preliminary Report on Patentability for PCT/US2021/061618, mailed on Jun. 15, 2023.

DEUTERATED FORMS OF TESTOSTERONE AND METHODS OF USE

CROSS REFERENCE TO RELATED APPLICATIONS

The present application is a continuation of and claims priority under 35 U.S.C. § 120 to U.S. patent application Ser. No. 17/556,859, filed Dec. 20, 2021, which claims priority under 35 U.S.C. § 120 to U.S. patent application Ser. No. 17/210,082, filed Mar. 23, 2021, which claims priority under 35 U.S.C. § 119(e) to U.S. Provisional Patent Application No. 63/121,766 filed Dec. 4, 2020, the entire contents of each of which are incorporated herein by reference.

BACKGROUND

Testosterone is a hormone found in humans and other animals. Testosterone is considered the most important male sex hormone (androgen). It is responsible for the normal growth and development of the male sex organs and for maintenance of secondary sex characteristics, including maturation of the prostate, seminal vesicles, penis, and scrotum; development of male hair distribution, such as beard, pubic, chest, and axillary hair; laryngeal enlargement; vocal cord thickening; alterations in body musculature; and fat distribution.

In humans, testosterone is metabolized by multiple pathways into various 17-keto steroids and sulfated or glucuronidated versions thereof. The major active metabolites of testosterone are estradiol and dihydrotestosterone (DHT). Testosterone is converted by aromatase (CYP19) into estradiol and by 5α-reductase into dihydrotestosterone (DHT). Estradiol is the main biologically active female sex hormone (estrogen). DHT is an androgen that is considerably more potent than testosterone as an agonist of the androgen receptor.

Numerous drug products have been approved by FDA that incorporate testosterone, or a testosterone prodrug, ester, derivative, or metabolite, as an active ingredient. These products have been approved as an androgen therapy for one or more of the following indications: (a) replacement therapy in adult males for conditions associated with a deficiency or absence of endogenous testosterone, specifically primary hypogonadism (congenital or acquired) and hypogonadotropic hypogonadism (congenital or acquired); (b) to stimulate puberty in carefully selected males with clearly delayed puberty; and (c) ablation of ovaries in women with metastatic mammary cancer.

Treatment with testosterone products, sometimes referred to as "testosterone replacement therapy" or "TRT," is known to cause or increase the risk of numerous, sometimes severe, side effects or adverse reactions, including: hypertension (increase in blood pressure); increase in heart rate; polycythemia; major adverse cardiovascular events, including myocardial infarction, stroke, and cardiovascular death; worsening of benign prostatic hyperplasia (BPH) and prostate cancer; venous thromboembolic events, including deep vein thrombosis (DVT) and pulmonary embolism (PE); adverse effects on spermatogenesis; hepatic adverse events (peliosis hepatis, hepatic neoplasms, cholestatic hepatitis, and jaundice), including hepatic adenoma with long term use; edema; gynecomastia; breast cancer; breast pain; sleep apnea; changes in serum lipid profile; hypercalcemia; decreased concentrations of thyroxin-binding globulin; and depression and suicidal ideation. Other side effects or adverse reactions may include: diarrhea, dyspepsia, eructation, peripheral edema, nausea, increased hematocrit, headache, and prostatomegaly.

Some of these side effects have been linked to the presence of high estrogen levels following testosterone therapy. Studies have indicated an association between increased estrogen levels following testosterone therapy to higher rates of heart attacks, strokes, and prostate cancer. See Tan et al., "High estrogen in men after injectable testosterone therapy: the low T experience," *Am J Men's Health*, 9(3):229-34 at 232 (2015). It has also been estimated that excess estrogen may result in gynecomastia and/or breast pain in between 10-25% of men on TRT. See Osterberg et al., "Risks of testosterone replacement therapy in men," *Indian J Urol.* 30(1):2-7 (2014).

Testosterone products are often co-administered with aromatase inhibitors, such as anastrozole, and selective estrogen receptor modulators (SERMs), such as tamoxifen, to mitigate certain side effects associated with increased estrogen levels. Aromatase inhibitors and SERMs are thought to lower the production of estradiol and mitigate some of the side effects associated with testosterone products, such as gynecomastia. It is reported that 30% of men who receive testosterone replacement therapy are co-administered an aromatase inhibitor or SERM. See Tan et al., "High estrogen in men after injectable testosterone therapy: the low T experience," *Am J Men's Health*, 9(3):229-34 (2015). However, aromatase inhibitors and SERMs are generally indicated for use as anti-cancer therapies, and not for use with testosterone products (i.e., they are used "off label" for these purposes), and come with additional, sometimes serious, side effects or adverse reactions.

There remains a significant need for safe and effective products comprising testosterone, or derivatives thereof, to treat a number of conditions and diseases.

SUMMARY OF THE INVENTION

The present invention relates to compounds (e.g., compounds of Formulae (I), (II), (III), or (IV)) and compositions (e.g., pharmaceutical compositions) comprising deuterated testosterone, deuterated methyltestosterone, or a derivative thereof. In certain embodiments, the composition further comprises a pharmaceutically acceptable carrier. In some embodiments, the composition is a solid dosage formulation (e.g., tablet, capsule, granule, powder, sachet, or chewable), solution, gel, suspension, emulsion, shampoo, conditioner, cream, foam, gel, lotion, ointment, transdermal patch, film, tincture, or paste. Further provided herein are methods and uses of the compositions described herein for treating a disease, preventing a disease, treating a condition, and/or preventing a condition. In certain embodiments, the disease or condition is hypogonadism, delay of growth and puberty, weight loss associated with HIV-associated wasting, vulvar dystrophies, micropenis, breast cancer, or a sexual disorder.

The compositions described herein comprise deuterated testosterone, deuterated methyltestosterone, or a derivative thereof (i.e., wherein at least one of the hydrogen atoms of testosterone, methyltestosterone, or a derivative thereof, is replaced with deuterium).

In one aspect, provided herein is a compound of Formula (I):

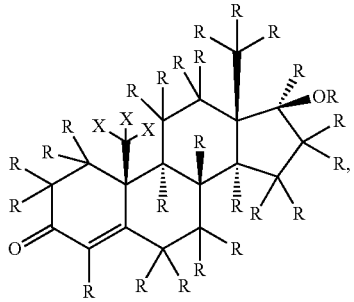

(I)

or a pharmaceutically acceptable salt, biologically active metabolite, solvate, hydrate, ester, prodrug, enantiomer or stereoisomer thereof, wherein X and R are as defined herein.

In another aspect, provided herein is a prodrug of the compound of Formula (I) having the structure of Formula (I-L):

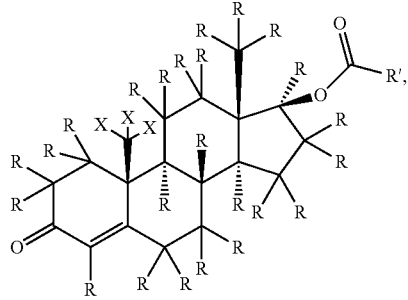

(I-L)

or a pharmaceutically acceptable salt, biologically active metabolite, solvate, hydrate, ester, prodrug, enantiomer or stereoisomer thereof, wherein X and R are as defined herein.

In another aspect, provided herein is a compound of Formula (II):

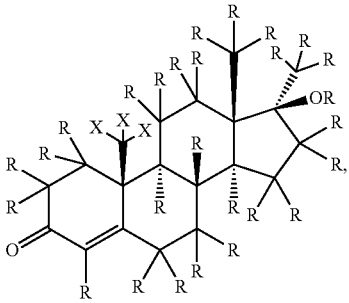

(II)

or a pharmaceutically acceptable salt, biologically active metabolite, solvate, hydrate, ester, prodrug, enantiomer or stereoisomer thereof, wherein X and R are as defined herein.

In another aspect, provided herein is a prodrug of the compound of Formula (II) having the structure of Formula (II-I):

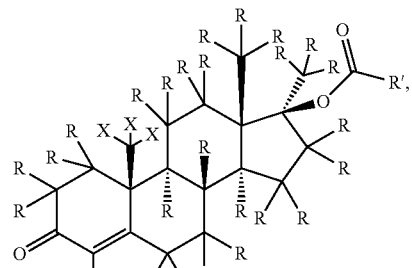

(II-I)

or a pharmaceutically acceptable salt, biologically active metabolite, solvate, hydrate, ester, prodrug, enantiomer or stereoisomer thereof, wherein X and R are as defined herein.

In another aspect, provided herein is a compound of Formula (III):

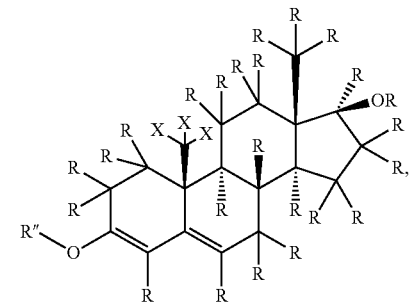

(III)

or a pharmaceutically acceptable salt, biologically active metabolite, solvate, hydrate, ester, prodrug, enantiomer or stereoisomer thereof, wherein R, X, $R^1$, and R" are as defined herein.

In another aspect, provided herein is a compound of Formula (IV):

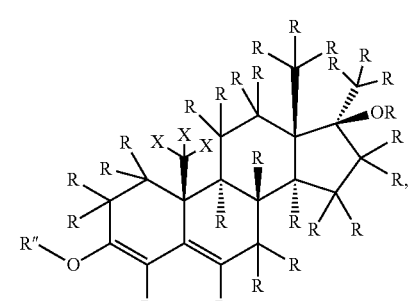

(IV)

or a pharmaceutically acceptable salt, biologically active metabolite, solvate, hydrate, ester, prodrug, enantiomer or stereoisomer thereof, wherein X, R, $R^1$, and R" are as defined herein.

In another aspect, provided herein is a composition comprising a compound disclosed herein.

In some embodiments, the subject matter disclosed herein provides a compound of Formula (I), or a pharmaceutically acceptable salt, biologically active metabolite, solvate, hydrate, ester, prodrug, enantiomer or stereoisomer thereof, wherein two instances of X are deuterium. In some embodiments, all instances of X are deuterium. In some embodiments, all instances of X are deuterium, and all instances of R are hydrogen (H). In some embodiments, the compound is a compound of Formula (I) wherein all instances of X are deuterium, and all instances of R are hydrogen (H), i.e., testosterone-19-d3 (Formula (I-d)).

In another aspect, provided herein is a pharmaceutical composition comprising an effective amount (e.g., a therapeutically effective amount) of a compound described herein, or a pharmaceutically acceptable salt, biologically active metabolite, solvate, hydrate, ester, prodrug, enantiomer or stereoisomer thereof.

In another aspect, the composition is a solid dose composition (e.g., tablet, capsule, granule, powder, sachet, or chewable). In another aspect, the composition is a solid dose composition suitable for oral administration. In another aspect, the composition is a solution or suspension suitable for oral administration. In another aspect, the composition is a sublingual film suitable for oral administration. In another aspect, the composition is a topical composition suitable for topical administration. In another aspect, the composition is suitable for nasal administration. In another aspect, the composition is suitable for parenteral administration (e.g., subcutaneous or intramuscular administration). In another aspect, the composition is suitable for administration by implantation. In another aspect, the composition is suitable for administration by injection.

The disclosure further provides kits comprising one or more compositions described herein, or composition components, and instructions for using the composition(s).

The disclosure further provides methods of treating or preventing a disease or condition in a subject in need thereof, comprising administering to the subject a compound of Formula (I), (II), (III), or (IV), or a pharmaceutically acceptable salt, biologically active metabolite, solvate, hydrate, ester, prodrug, enantiomer or stereoisomer thereof. In certain embodiments, the method is for treating a disease or condition. In certain embodiments, the method is for preventing a disease or condition.

In another aspect, the present disclosure provides methods of treating or preventing a disease that is responsive to an androgen agonist therapy in a subject in need thereof, while avoiding one or more side effects associated with the administration of non-isotopically enriched testosterone, the method comprising administering to the subject an effective amount (e.g., a therapeutically effective amount or a prophylactically effective amount) of a compound or composition (e.g., a pharmaceutical composition) of the present disclosure.

In another aspect, provided herein is a method of determining the effect of a compound provided herein (e.g., a compound of Formula (I), (II), (III), or (IV)), or a pharmaceutically acceptable salt, biologically active metabolite, solvate, hydrate, ester, prodrug, enantiomer or stereoisomer thereof, or a pharmaceutical composition thereof, following administration of the compound or composition to a subject in need thereof, comprising administering the compound to the subject, and detecting the level, or change in the level, of endogenous testosterone, or one or more metabolites thereof, or of the compound, or one or more metabolites thereof, in the subject. In certain embodiments, the method further comprises determining the optimal dosage, timing, or formulation for a subsequent administration of the compound or composition, and optionally, administering a subsequent dose of the compound or composition to the subject.

The details of one or more embodiments of the present disclosure are set forth herein. Other features, objects, and advantages of the present disclosure will be apparent from the Detailed Description, Examples, and Claims.

DEFINITIONS

Figure 1A:
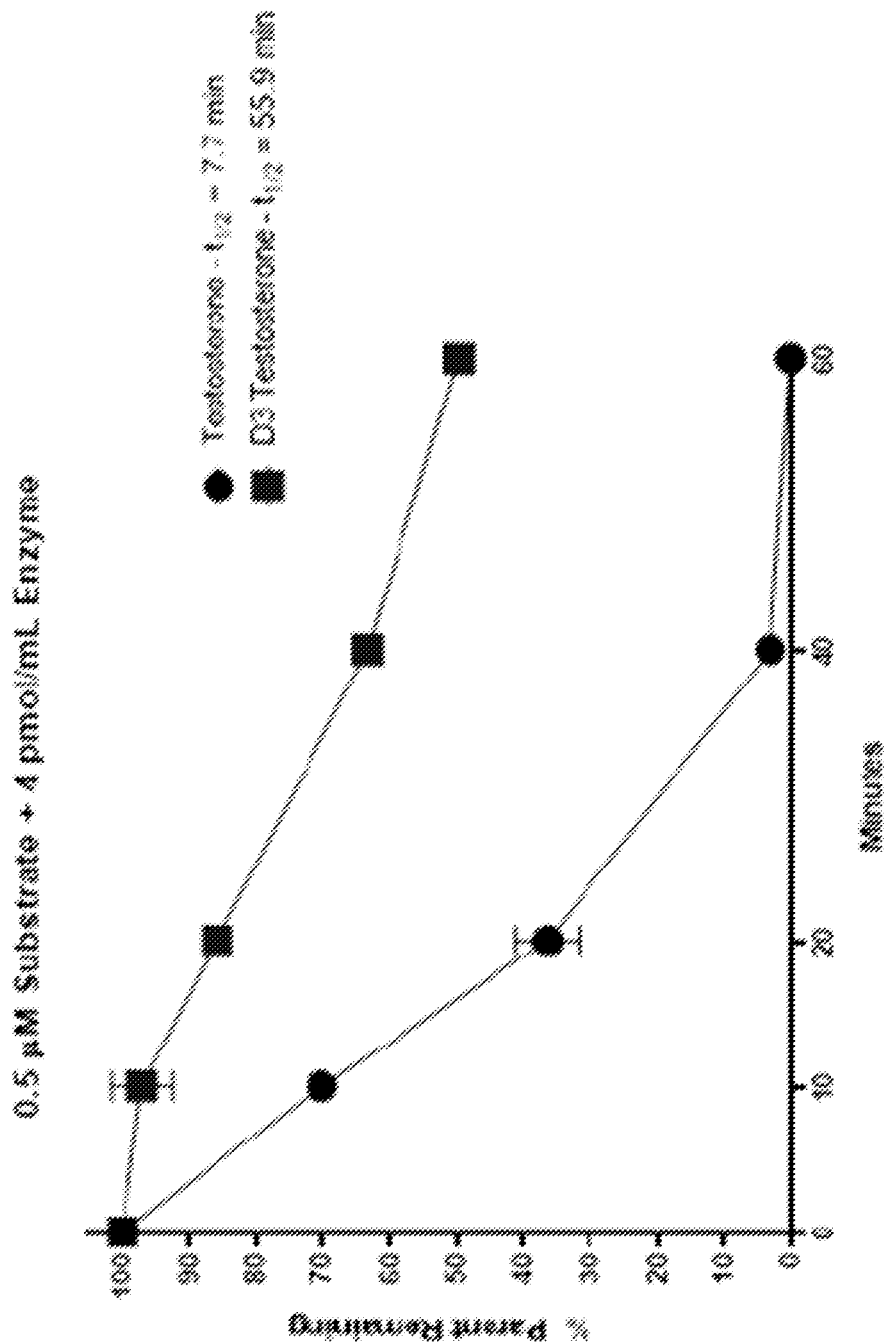
FIGS. 1A-B shows the result of a metabolic stability study of testosterone (FIG. 1A) and testosterone-19-d3 (FIG. 1B; Formula (I-d)) in the presence of an aromatase.

Before further description of the present invention, and in order that the invention may be more readily understood, certain terms are first defined and collected here for convenience.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high-pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R·x H$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R·0.5H$_2$O)), and polyhydrates (x is a number greater than 1, e.g., dihydrates (R·2H$_2$O) and hexahydrates (R·6H$_2$O)).

"Prodrug" or "pharmaceutically acceptable prodrug" refers to a compound that is metabolized, for example hydrolyzed or oxidized, in the host after administration to form the compound of the present disclosure (e.g., compounds of Formula (I), (II), (III), or (IV)). The present disclosure includes within its scope, prodrugs of the compounds described herein. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred. Examples of prodrugs of testosterone include, but are not limited to, testosterone undecanoate, testosterone cypionate, testosterone enanthate, testosterone propionate, and testosterone buciclate. Conventional procedures for the selection and preparation of suitable prodrugs are described, for example, in "Design of Prodrugs" Ed. H. Bundgaard, Elsevier, 1985. As used herein, "prodrug" may also refer to a naturally occurring precursor of testosterone, such as androstenedione.

Where the compound disclosed herein is an ester (e.g., testosterone acetate) or prodrug of a compound of Formula (I), (II), (III), or (IV) (e.g., testosterone undecanoate), it is understood that the ester or prodrug component (e.g., for testosterone undecanoate, the undecylate ester) may comprise additional instances of hydrogen, when not isotopically enriched, that are not depicted in the drawing of Formula (I), (II), (III), or (IV). In certain embodiments, the ester and prodrug components are not isotopically enriched. In certain embodiments, the ester and prodrug components are partially or fully deuterated.

The term "biologically active metabolite" means a pharmacologically active product produced through metabolism in the body of a specified compound (e.g., a compound of Formula (I), (II), (III), or (IV)) or salt thereof.

The term "isotopes" refers to variants of a particular chemical element such that, while all isotopes of a given element share the same number of protons in each atom of the element, those isotopes differ in the number of neutrons.

The terms "treatment," "treat," and "treating" refer to reversing, alleviating, delaying the onset of, or inhibiting the progress of a disease or condition described herein, or to reversing, alleviating, delaying the onset of, or inhibiting the symptoms of a disease or condition described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence of a disease or condition.

The term "administer," "administering," or "administration" refers to implanting, absorbing, ingesting, injecting, inhaling, or otherwise introducing a compound described herein, or a composition thereof, in or on a subject.

The terms "condition," "disease," and "disorder" are used interchangeably.

The terms "composition" and "formulation" are used interchangeably.

The term "total amount of testosterone" refers to the combined total amount of deuterated testosterone and non-isotopically enriched testosterone. The term "total amount of methyltestosterone" refers to the combined total amount of deuterated methyltestosterone and non-isotopically enriched methyltestosterone.

The amount of an active agent (e.g., deuterated testosterone or a derivative thereof) or combination of active agents thereof included in a provided composition or nutritional supplement described herein will depend on the target population. In some embodiments, a provided composition or nutritional supplement contains an effective amount of an active agent (e.g., deuterated testosterone or a derivative thereof). The term "effective amount," as used herein, refers to a sufficient amount of the active agent (e.g., deuterated testosterone or a derivative thereof) to produce a desired outcome. The exact amount required will vary from subject to subject, depending on the species, age, general condition of the subject, and the indication. The term "therapeutically effective amount" as used herein refers to a sufficient amount of a pharmaceutical agent (e.g., deuterated testosterone or a derivative thereof) to achieve the intended purpose, such as, for example, to cause a reduction of symptoms of a condition or disease. A "prophylactically effective amount" refers to a sufficient amount of a pharmaceutical agent (e.g., deuterated testosterone or a derivative thereof) to achieve the intended purpose, such as prevention of a condition or disease, one or more symptoms associated with the condition or disease, and/or the recurrence thereof. In certain embodiments, an effective amount of a composition or nutritional supplement is the effective amount of the active agent (e.g., deuterated testosterone or a derivative thereof) included in the composition or nutritional supplement.

The phrase "same or equivalent amount," as used herein refers to amounts as measured by mass or by moles, respectively.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease.

The term "half-life" refers to a biological half-life of a particular compound in vivo. Half-life ($t_{1/2}$) may be expressed as the time required for elimination of half of the dose administered to a subject from the blood and/or other tissues, that is, the time required for the maximum concentration to decrease to half maximum concentration. Half-life is typically used when the rate of removal is approximately exponential. In some embodiments, half-life may be measured by monitoring plasma concentration over time after intravenous administration of a single weight-based dose.

When a range of values ("range") is listed, it encompasses each value and sub-range within the range. A range is inclusive of the values at the two ends of the range unless otherwise provided. It will be understood that when a range is recited in the application, the ends of the range are specifically disclosed as if specifically recited. For example, a range of about 19% to about 99% specifically include a disclosure separately of 19% and separately of 99%.

DETAILED DESCRIPTION OF CERTAIN EMBODIMENTS OF THE INVENTION

The present disclosure relates to compounds and compositions comprising deuterated testosterone, deuterated methyltestosterone, or derivatives thereof (e.g., compounds of Formula (I), (II), (III), or (IV)). Also provided herein are kits containing the compositions and instructions for use. Further provided herein are methods and uses of any of the compounds or compositions described herein for treating a disease, preventing a disease, treating a condition, preventing a condition, and/or causing an effect.

Compounds

In one aspect, provided herein is a compound of Formula (I):

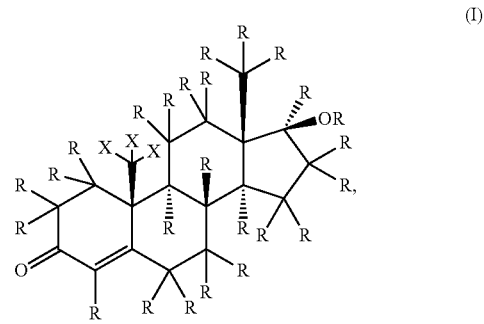

or a pharmaceutically acceptable salt, biologically active metabolite, solvate, hydrate, ester, prodrug, enantiomer or stereoisomer thereof;

wherein each R is independently hydrogen or deuterium;
wherein each X is independently hydrogen or deuterium; and
wherein at least one instance of X is deuterium.

In some embodiments of Formula (I), one instance of X is deuterium. In some embodiments, two instances of X are deuterium. In some embodiments, at least two instances of X are deuterium. In some embodiments, all instances of X are deuterium.

In some embodiments of Formula (I), all instances of R are hydrogen (H). In some embodiments, at least one instance of R is H. In some embodiments, at least two instances of R are H. In some embodiments, at least three instances of R are H. In some embodiments, at least four instances of R are H. In some embodiments, at least five instances of R are H. In some embodiments, at least six instances of R are H. In some embodiments, at least seven instances of R are H. In some embodiments, at least eight instances of R are H. In some embodiments, at least nine instances of R are H. In some embodiments, at least ten instances of R are H. In some embodiments, at least eleven instances of R are H. In some embodiments, at least twelve instances of R are H. In some embodiments, at least thirteen instances of R are H. In some embodiments, at least fourteen instances of R are H. In some embodiments, at least fifteen instances of R are H. In some embodiments, at least sixteen instances of R are H. In some embodiments, at least seventeen instances of R are H. In some embodiments, at least eighteen instances of R are H. In some embodiments, at least nineteen instances of R are H. In some embodiments, at least twenty instances of R are H. In some embodiments, at least twenty-one instances of R are H. In some embodiments, at least twenty-two instances of R are H. In some embodiments, at least twenty-three instances of R are H. In some embodiments, at least twenty-four instances of R are H.

In some embodiments of Formula (I), at least one instance of R is deuterium. In some embodiments, two to ten instances of R are deuterium. In some embodiments, up to fifteen instances of R are deuterium. In some embodiments, up to twenty instances of R are deuterium. In some embodiments, all instances of R are deuterium.

In some embodiments, two instances of R are deuterium. In some embodiments, three instances of R are deuterium. In some embodiments, four instances of R are deuterium. In some embodiments, five instances of R are deuterium. In some embodiments, six instances of R are deuterium. In some embodiments, seven instances of R are deuterium. In some embodiments, eight instances of R are deuterium. In some embodiments, nine instances of R are deuterium. In some embodiments, ten instances of R are deuterium. In some embodiments, eleven instances of R are deuterium. In some embodiments, twelve instances of R are deuterium. In some embodiments, thirteen instances of R are deuterium. In some embodiments, fourteen instances of R are deuterium. In some embodiments, fifteen instances of R are deuterium. In some embodiments, sixteen instances of R are deuterium. In some embodiments, seventeen instances of R are deuterium. In some embodiments, eighteen instances of R are deuterium. In some embodiments, nineteen instances of R are deuterium. In some embodiments, twenty instances of R are deuterium. In some embodiments, twenty-one instances of R are deuterium. In some embodiments, twenty-two instances of R are deuterium. In some embodiments, twenty-three instances of R are deuterium. In some embodiments, twenty-four instances of R are deuterium.

In some embodiments of Formula (I), all instances of X are deuterium, and all instances of R are hydrogen (H), i.e., testosterone-19-d3 (Formula (I-d)). In some embodiments, the compound of Formula (I) is not testosterone-19-d3 (Formula (I-d)). In some embodiments, the compound is a prodrug of the compound of Formula (I), for example an ester such as undecanoate, cypionate, enanthate, propionate, or buciclate, wherein all instances of X are deuterium, all other instances of R are H, and the prodrug component (e.g., an alkanoate moiety) contains no more than a naturally-occurring amount of deuterium. In certain embodiments, the prodrug component may be partially or fully isotopically enriched with deuterium.

In certain embodiments, the compound of Formula (I) is of Formula (I-A):

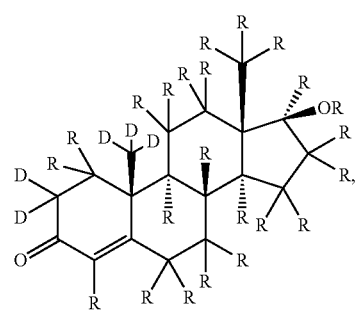

(I-A)

or a pharmaceutically acceptable salt, biologically active metabolite, solvate, hydrate, ester, prodrug, enantiomer or stereoisomer thereof.

In certain embodiments, the compound of Formula (I) is of Formula (I-B):

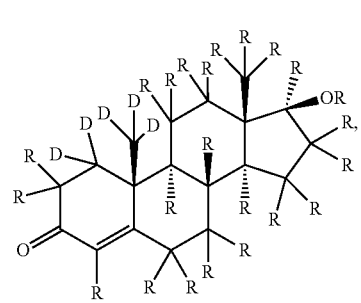

(I-B)

or a pharmaceutically acceptable salt, biologically active metabolite, solvate, hydrate, ester, prodrug, enantiomer or stereoisomer thereof.

In certain embodiments, the compound of Formula (I) is of Formula (I-C):

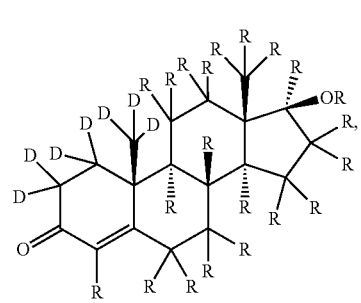

(I-C)

or a pharmaceutically acceptable salt, biologically active metabolite, solvate, hydrate, ester, prodrug, enantiomer or stereoisomer thereof.

In certain embodiments, the compound of Formula (I) is of Formula (I-D):

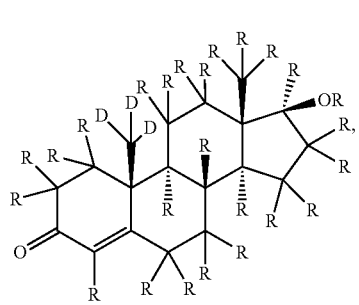

(I-D)

or a pharmaceutically acceptable salt, biologically active metabolite, solvate, hydrate, ester, prodrug, enantiomer or stereoisomer thereof.

In certain embodiments, the compound of Formula (I) is of Formula (I-E):

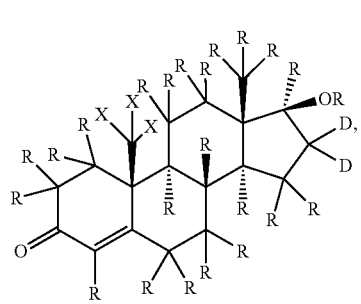

(I-E)

or a pharmaceutically acceptable salt, biologically active metabolite, solvate, hydrate, ester, prodrug, enantiomer or stereoisomer thereof. In particular embodiments, one, two, or three instances of X are deuterium.

In certain embodiments, the compound of Formula (I) is of Formula (I-F):

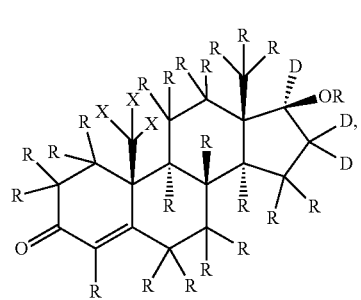

(I-F)

or a pharmaceutically acceptable salt, biologically active metabolite, solvate, hydrate, ester, prodrug, enantiomer or stereoisomer thereof. In particular embodiments, one, two, or three instances of X are deuterium.

In certain embodiments, the compound of Formula (I) is of Formula (I-G):

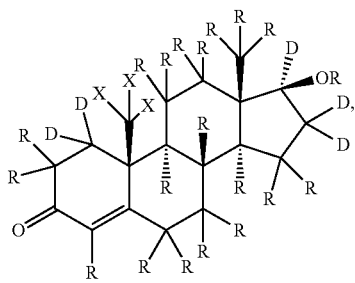

(I-G)

or a pharmaceutically acceptable salt, biologically active metabolite, solvate, hydrate, ester, prodrug, enantiomer or stereoisomer thereof. In particular embodiments, one, two, or three instances of X are deuterium.

In certain embodiments, the compound of Formula (I) is of Formula (I-H):

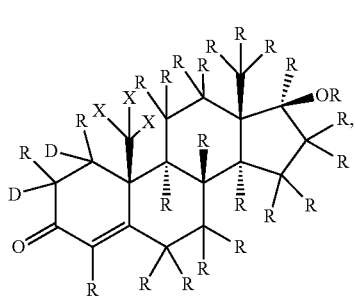

(I-H)

or a pharmaceutically acceptable salt, biologically active metabolite, solvate, hydrate, ester, prodrug, enantiomer or stereoisomer thereof. In particular embodiments, one, two, or three instances of X are deuterium.

In certain embodiments, the compound of Formula (I) is of Formula (I-I):

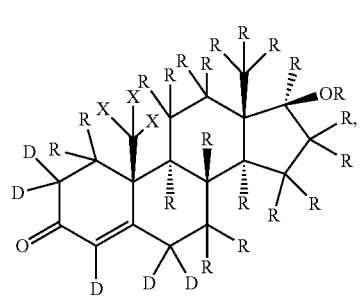

(I-I)

or a pharmaceutically acceptable salt, biologically active metabolite, solvate, hydrate, ester, prodrug, enantiomer or stereoisomer thereof. In particular embodiments, one, two, or three instances of X are deuterium.

In certain embodiments, the compound of Formula (I) is of Formula (I-J):

(I-J)

or a pharmaceutically acceptable salt, biologically active metabolite, solvate, hydrate, ester, prodrug, enantiomer or stereoisomer thereof. In particular embodiments, one, two, or three instances of X are deuterium.

In certain embodiments, the compound of Formula (I) is of Formula (I-K):

(I-K)

or a pharmaceutically acceptable salt, biologically active metabolite, solvate, hydrate, ester, prodrug, enantiomer or stereoisomer thereof. In particular embodiments, one, two, or three instances of X are deuterium.

In certain embodiments, the compound of Formula (I) is selected from the group consisting of:

(I-a)

(I-b)

(I-c)

(I-d)

"Testosterone-19-d3"

and pharmaceutically acceptable salts, biologically active metabolites, solvates, hydrates, esters, prodrugs, enantiomers, and stereoisomers thereof. In certain embodiments, the compound of Formula (I) is not (I-d).

In certain embodiments, the compound of Formula (I) is selected from the group consisting of:

(I-e)

(I-f)

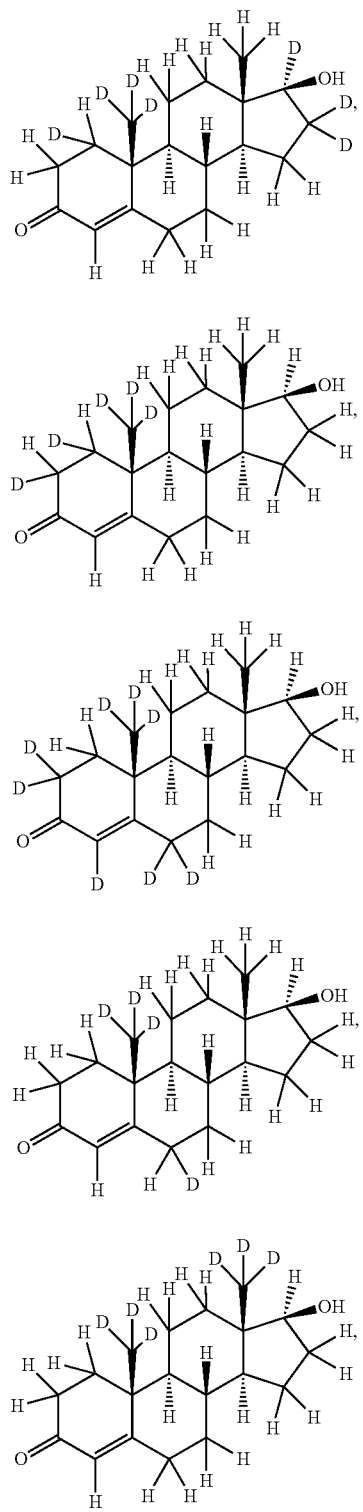

(I-g)

(I-h)

(I-i)

(I-j)

(I-k)

and pharmaceutically acceptable salts, biologically active metabolites, solvates, hydrates, esters, prodrugs, enantiomers, and stereoisomers thereof.

In an embodiment, provided herein is a prodrug of the compound of Formula (I) having the structure of Formula (I-L):

(I-L)

or a pharmaceutically acceptable salt, biologically active metabolite, solvate, hydrate, ester, prodrug, enantiomer or stereoisomer thereof;
  wherein each R is independently hydrogen or deuterium;
  wherein each X is independently hydrogen or deuterium;
  wherein at least one instance of X is deuterium;
  wherein R' is $C_{1-20}$ branched or unbranched aliphatic, branched or unbranched heteroaliphatic, carbocyclic, heterocyclic, aromatic, heteroaromatic, or any combination thereof; and
  wherein each non-carbon atom or non-heteroatom substituent of R' is independently hydrogen or deuterium.

In some embodiments of Formula (I-L), one instance of X is deuterium. In some embodiments, two instances of X are deuterium. In some embodiments, at least two instances of X are deuterium. In some embodiments, all instances of X are deuterium.

In some embodiments of Formula (I), all instances of R are hydrogen (H). In some embodiments, at least one instance of R is H. In some embodiments, at least two instances of R are H. In some embodiments, at least three instances of R are H. In some embodiments, at least four instances of R are H. In some embodiments, at least five instances of R are H. In some embodiments, at least six instances of R are H. In some embodiments, at least seven instances of R are H. In some embodiments, at least eight instances of R are H. In some embodiments, at least nine instances of R are H. In some embodiments, at least ten instances of R are H. In some embodiments, at least eleven instances of R are H. In some embodiments, at least twelve instances of R are H. In some embodiments, at least thirteen instances of R are H. In some embodiments, at least fourteen instances of R are H. In some embodiments, at least fifteen instances of R are H. In some embodiments, at least sixteen instances of R are H. In some embodiments, at least seventeen instances of R are H. In some embodiments, at least eighteen instances of R are H. In some embodiments, at least nineteen instances of R are H. In some embodiments, at least twenty instances of R are H. In some embodiments, at least twenty-one instances of R are H. In some embodiments, at least twenty-two instances of R are H. In some embodiments, at least twenty-three instances of R are H. In some embodiments, at least twenty-four instances of R are H.

In some embodiments of Formula (I-L), at least one instance of R is deuterium. In some embodiments, two to ten instances of R are deuterium. In some embodiments, up to fifteen instances of R are deuterium. In some embodiments, up to twenty instances of R are deuterium. In some embodiments, all instances of R are deuterium.

In some embodiments, two instances of R are deuterium. In some embodiments, three instances of R are deuterium. In some embodiments, four instances of R are deuterium. In some embodiments, five instances of R are deuterium. In some embodiments, six instances of R are deuterium. In some embodiments, seven instances of R are deuterium. In some embodiments, eight instances of R are deuterium. In some embodiments, nine instances of R are deuterium. In some embodiments, ten instances of R are deuterium. In some embodiments, eleven instances of R are deuterium. In some embodiments, twelve instances of R are deuterium. In some embodiments, thirteen instances of R are deuterium. In some embodiments, fourteen instances of R are deuterium. In some embodiments, fifteen instances of R are deuterium. In some embodiments, sixteen instances of R are deuterium. In some embodiments, seventeen instances of R are deuterium. In some embodiments, eighteen instances of R are deuterium. In some embodiments, nineteen instances of R are deuterium. In some embodiments, twenty instances of R are deuterium. In some embodiments, twenty-one instances of R are deuterium. In some embodiments, twenty-two instances of R are deuterium. In some embodiments, twenty-three instances of R are deuterium. In some embodiments, twenty-four instances of R are deuterium.

In certain embodiments, the ester of Formula (I-L) is a caproate, cypionate, decanoate, enanthate, isobutyrate, isocaproate, phenylpropionate, propionate, or undecenoate ester. In some embodiments, the ester of Formula (I-L) is a cyclohexylpropionate, acetate, enantate benzylic acid hydrzone, furoate, hexahydrobenzoate, hexahydrobenzylcarbonate, hexahydrophenylpropionate, ketolaurate, nicotinate, phenylacetate, phosphate, undecylenate, or valerate ester. In certain embodiments, the ester of Formula (I-L) is a buciclate, benzoate, butyrate, formate, isovalerate, palmitate, phenylbutyrate, or stearate ester. In some embodiments, the compound of Formula (I-L) is not a propionate ester.

In certain embodiments, Formula (I-L) is selected from the group consisting of:

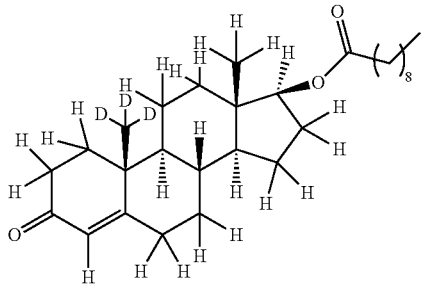

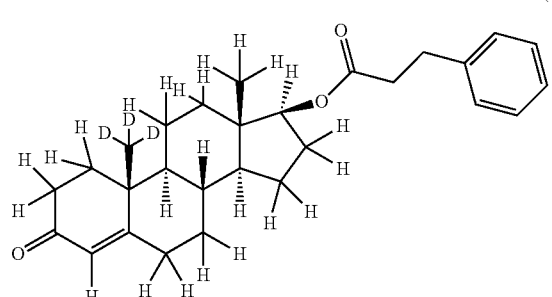

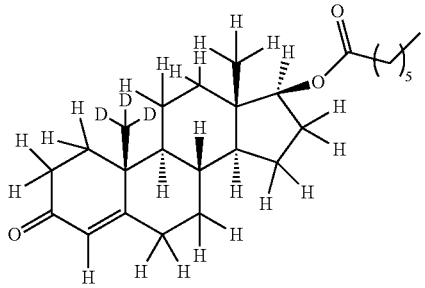

-continued (I-s)
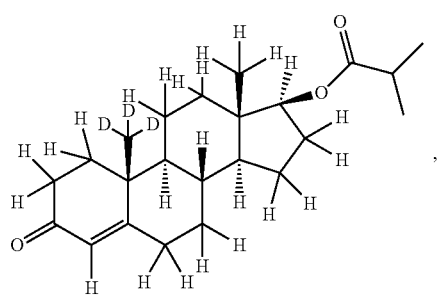

(I-t)
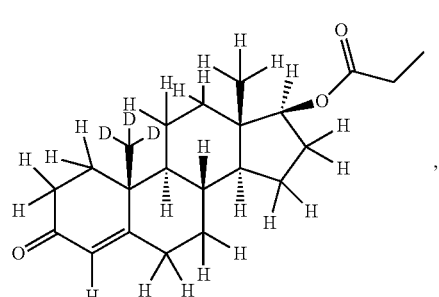

(I-u)
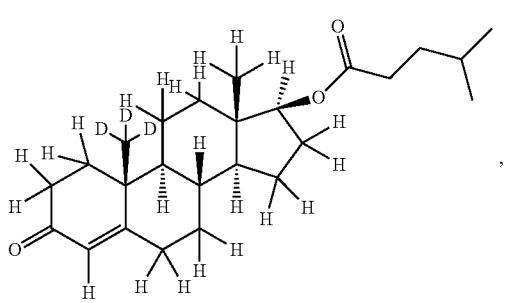

or a pharmaceutically acceptable salt, biologically active metabolite, solvate, hydrate, ester, prodrug, enantiomer, or stereoisomer thereof.

In another aspect, provided herein is a compound of Formula (I-M):

(I-M)
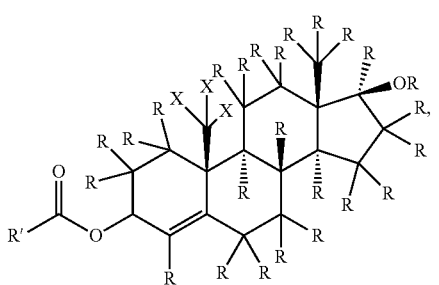

or a pharmaceutically acceptable salt, biologically active metabolite, solvate, hydrate, ester, prodrug, enantiomer or stereoisomer thereof;
  wherein each R is independently hydrogen or deuterium;
  wherein each X is independently hydrogen or deuterium;
  wherein at least one instance of X is deuterium;
  wherein R' is $C_{1-20}$ branched or unbranched aliphatic, branched or unbranched heteroaliphatic, carbocyclic, heterocyclic, aromatic, heteroaromatic, or any combination thereof; and wherein each non-carbon atom or non-heteroatom substituent of R' is independently hydrogen or deuterium.

In another aspect, provided herein is a compound of Formula (I-N):

(I-N)
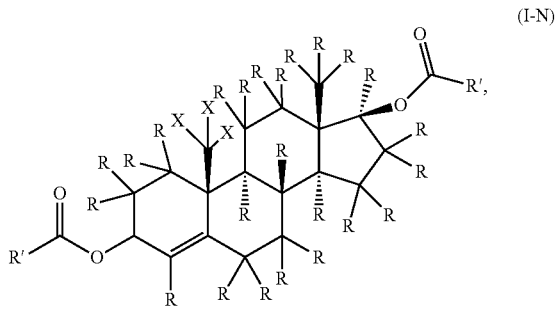

or a pharmaceutically acceptable salt, biologically active metabolite, solvate, hydrate, ester, prodrug, enantiomer or stereoisomer thereof;
  wherein each R is independently hydrogen or deuterium;
  wherein each X is independently hydrogen or deuterium;
  wherein at least one instance of X is deuterium;
  wherein each instance of R' is independently $C_{1-20}$ branched or unbranched aliphatic, branched or unbranched heteroaliphatic, carbocyclic, heterocyclic, aromatic, heteroaromatic, or any combination thereof; and
  wherein each non-carbon atom or non-heteroatom substituent of each instance of R' is independently hydrogen or deuterium.

In certain embodiments of Formulae (I-L), (I-M), and (I-N), R' is $C_{1-20}$ branched or unbranched aliphatic, branched or unbranched heteroaliphatic, carbocyclic, heterocyclic, aromatic, heteroaromatic, or any combination thereof. In certain embodiments, R' is $C_{1-20}$ branched or unbranched aliphatic, carbocyclic, aromatic, or any combination thereof. In certain embodiments, R' is $C_{1-20}$ branched or unbranched heteroaliphatic, heterocyclic, heteroaromatic, or any combination thereof. In some embodiments, R' comprises $C_{1-20}$ branched or unbranched aliphatic. In certain embodiments, R' comprises $C_{1-20}$ branched aliphatic. In some embodiments, R' comprises $C_{1-20}$ unbranched aliphatic. In certain embodiments, R' comprises $C_{1-20}$ branched or unbranched alkyl. In certain embodiments, R' comprises $C_{1-10}$ branched or unbranched alkyl. In certain embodiments, R' comprises $C_{1-20}$ branched or unbranched heteroaliphatic. In some embodiments, R' comprises $C_{1-20}$ carbocyclic. In certain embodiments, R' comprises $C_{1-10}$ carbocyclic. In certain embodiments, R' comprises $C_{1-7}$ carbocyclic. In certain embodiments, R' comprises $C_{1-20}$ heterocyclic. In certain embodiments, R' comprises $C_{1-20}$ aromatic. In certain embodiments, R' comprises $C_{1-10}$ aromatic In certain embodiments, R' comprises $C_{1-20}$ heteroaromatic. In certain embodiments, R' is methyl, ethyl, propyl, or butyl. In certain embodiments, R' is cyclopropyl, cyclobutyl, cyclopentyl, cyclohexyl, or cycloheptyl.

In another aspect, provided herein is a compound of Formula (II):

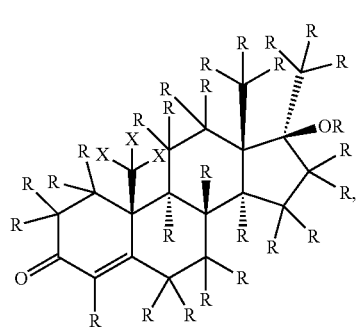

(II)

or a pharmaceutically acceptable salt, biologically active metabolite, solvate, hydrate, ester, prodrug, enantiomer or stereoisomer hereof;
wherein each R is independently hydrogen or deuterium;
wherein each X is independently hydrogen or deuterium; and
wherein at least one instance of X is deuterium.

In some embodiments of Formula (II), one instance of X is deuterium. In some embodiments, two instances of X are deuterium. In some embodiments, at least two instances of X are deuterium. In some embodiments, all instances of X are deuterium.

In some embodiments of Formula (II), all instances of R are hydrogen (H). In some embodiments, at least one instance of R is H. In some embodiments, at least two instances of R are H. In some embodiments, at least three instances of R are H. In some embodiments, at least four instances of R are H. In some embodiments, at least five instances of R are H. In some embodiments, at least six instances of R are H. In some embodiments, at least seven instances of R are H. In some embodiments, at least eight instances of R are H. In some embodiments, at least nine instances of R are H. In some embodiments, at least ten instances of R are H. In some embodiments, at least eleven instances of R are H. In some embodiments, at least twelve instances of R are H. In some embodiments, at least thirteen instances of R are H. In some embodiments, at least fourteen instances of R are H. In some embodiments, at least fifteen instances of R are H. In some embodiments, at least sixteen instances of R are H. In some embodiments, at least seventeen instances of R are H. In some embodiments, at least eighteen instances of R are H. In some embodiments, at least nineteen instances of R are H. In some embodiments, at least twenty instances of R are H. In some embodiments, at least twenty-one instances of R are H. In some embodiments, at least twenty-two instances of R are H. In some embodiments, at least twenty-three instances of R are H. In some embodiments, at least twenty-four instances of R are H. In some embodiments, at least twenty-five instances of R are H. In some embodiments, at least twenty-six instances of R are H.

In some embodiments of Formula (II), at least one instance of R is deuterium. In some embodiments, two to ten instances of R are deuterium. In some embodiments, up to fifteen instances of R are deuterium. In some embodiments, up to twenty instances of R are deuterium. In some embodiments, all instances of R are deuterium.

In some embodiments, two instances of R are deuterium. In some embodiments, three instances of R are deuterium. In some embodiments, four instances of R are deuterium. In some embodiments, five instances of R are deuterium. In some embodiments, six instances of R are deuterium. In some embodiments, seven instances of R are deuterium. In some embodiments, eight instances of R are deuterium. In some embodiments, nine instances of R are deuterium. In some embodiments, ten instances of R are deuterium. In some embodiments, eleven instances of R are deuterium. In some embodiments, twelve instances of R are deuterium. In some embodiments, thirteen instances of R are deuterium. In some embodiments, fourteen instances of R are deuterium. In some embodiments, fifteen instances of R are deuterium. In some embodiments, sixteen instances of R are deuterium. In some embodiments, seventeen instances of R are deuterium. In some embodiments, eighteen instances of R are deuterium. In some embodiments, nineteen instances of R are deuterium. In some embodiments, twenty instances of R are deuterium. In some embodiments, twenty-one instances of R are deuterium. In some embodiments, twenty-two instances of R are deuterium. In some embodiments, twenty-three instances of R are deuterium. In some embodiments, twenty-four instances of R are deuterium. In some embodiments, twenty-five instances of R are deuterium. In some embodiments, twenty-six instances of R are deuterium.

In certain embodiments, the compound of Formula (II) is of Formula (II-A):

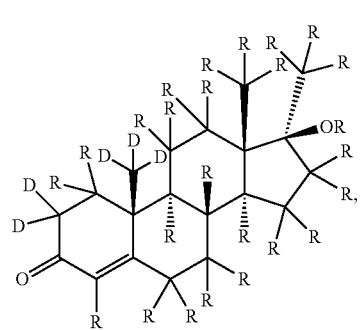

(II-A)

or a pharmaceutically acceptable salt, biologically active metabolite, solvate, hydrate, ester, prodrug, enantiomer or stereoisomer thereof.

In certain embodiments, the compound of Formula (II) is of Formula (II-B):

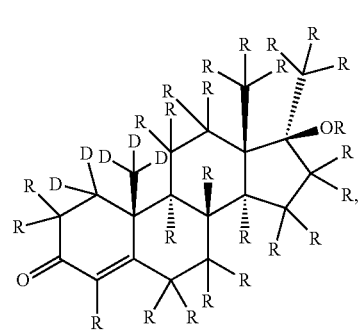

(II-B)

or a pharmaceutically acceptable salt, biologically active metabolite, solvate, hydrate, ester, prodrug, enantiomer or stereoisomer thereof.

In certain embodiments, the compound of Formula (II) is of Formula (II-C):

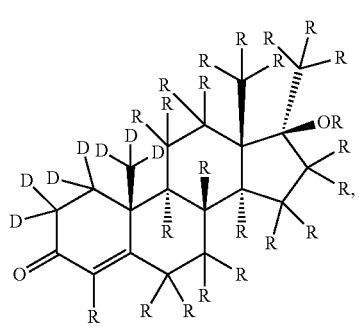
(II-C)

or a pharmaceutically acceptable salt, biologically active metabolite, solvate, hydrate, ester, prodrug, enantiomer or stereoisomer thereof.

In certain embodiments, the compound of Formula (II) is of Formula (II-D):

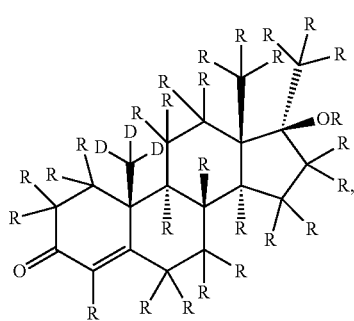
(II-D)

or a pharmaceutically acceptable salt, biologically active metabolite, solvate, hydrate, ester, prodrug, enantiomer or stereoisomer thereof.

In certain embodiments, the compound of Formula (II) is of Formula (II-E):

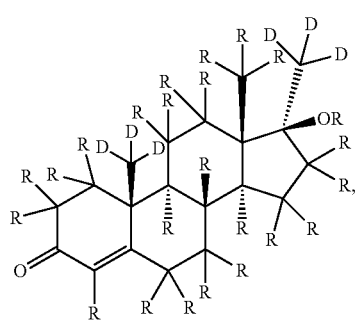
(II-E)

or a pharmaceutically acceptable salt, biologically active metabolite, solvate, hydrate, ester, prodrug, enantiomer or stereoisomer thereof.

In certain embodiments, the compound of Formula (II) is of Formula (II-F):

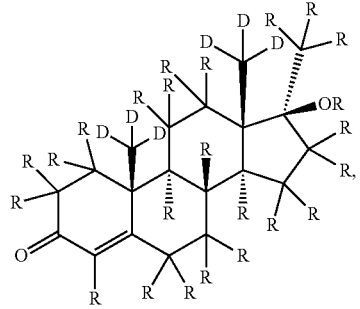
(II-F)

or a pharmaceutically acceptable salt, biologically active metabolite, solvate, hydrate, ester, prodrug, enantiomer or stereoisomer thereof.

In certain embodiments, the compound of Formula (II) is of Formula (II-G):

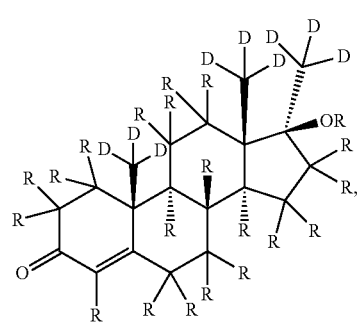
(II-G)

or a pharmaceutically acceptable salt, biologically active metabolite, solvate, hydrate, ester, prodrug, enantiomer or stereoisomer thereof.

In certain embodiments, the compound of Formula (II) is of Formula (II-H):

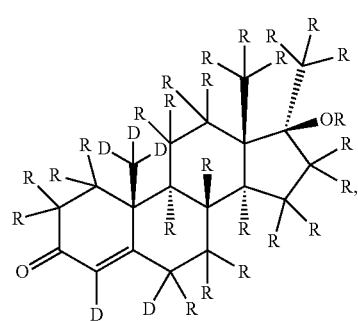
(II-H)

or a pharmaceutically acceptable salt, biologically active metabolite, solvate, hydrate, ester, prodrug, enantiomer or stereoisomer thereof.

In certain embodiments, the compound of Formula (II) is selected from:

(II-a)
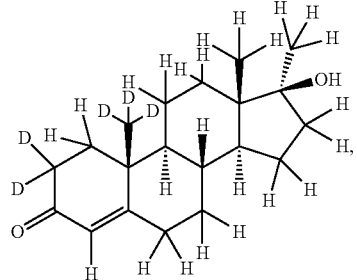

(II-b)
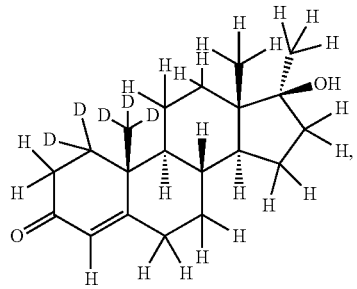

(II-c)
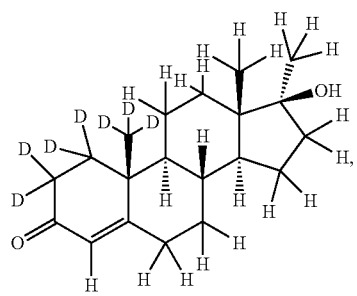

(II-d)
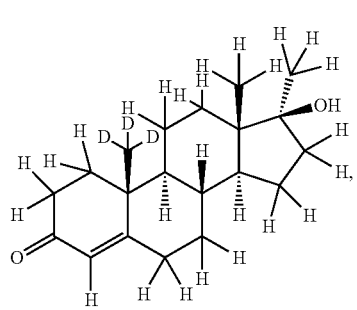

(II-e)
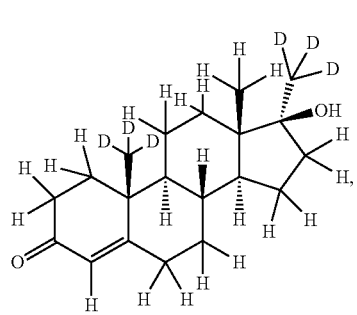

(II-f), (II-g), (II-h)
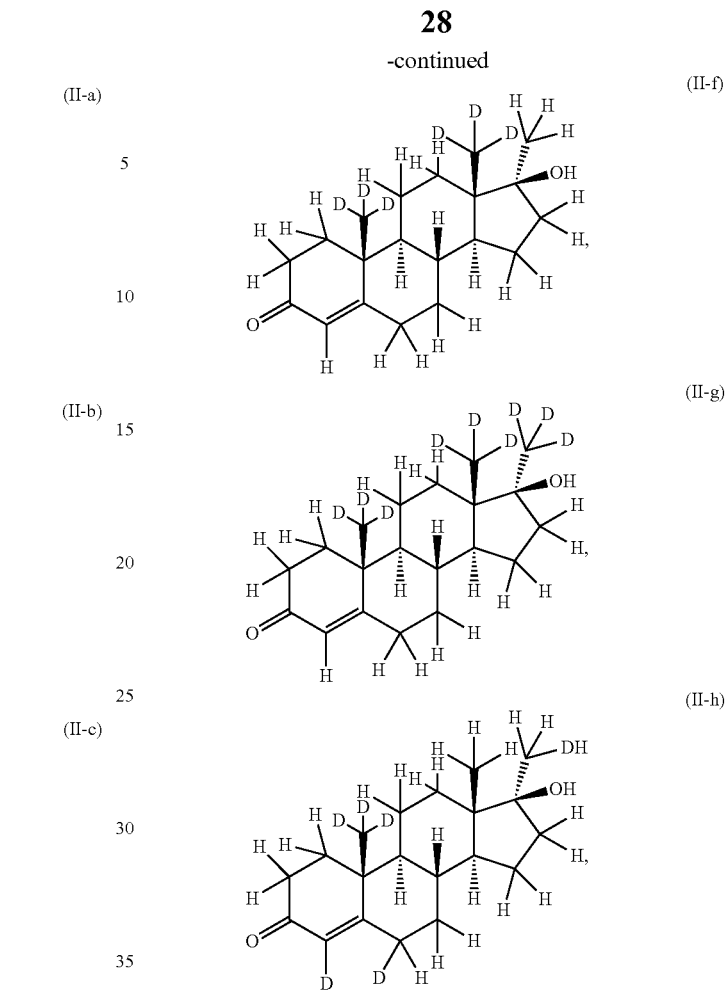

or a pharmaceutically acceptable salt, biologically active metabolite, solvate, hydrate, ester, prodrug, enantiomer or stereoisomer thereof.

In an embodiment, provided herein is a prodrug of the compound of Formula (II) having the structure of Formula (II-I):

(II-I)
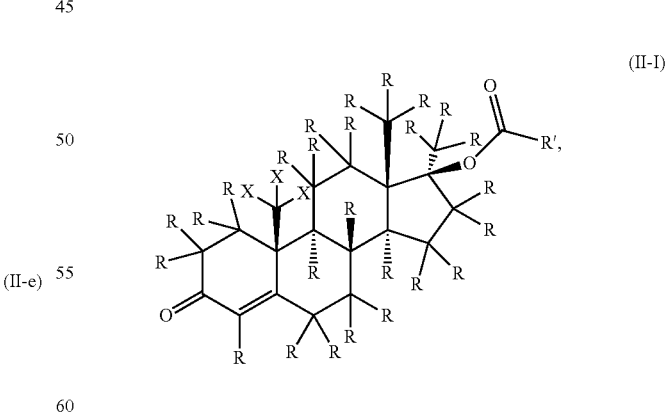

or a pharmaceutically acceptable salt, biologically active metabolite, solvate, hydrate, ester, prodrug, enantiomer or stereoisomer thereof;

wherein each R is independently hydrogen or deuterium;
wherein each X is independently hydrogen or deuterium;
wherein at least one instance of X is deuterium;

wherein R' is $C_{1-20}$ branched or unbranched aliphatic, branched or unbranched heteroaliphatic, carbocyclic, heterocyclic, aromatic, heteroaromatic, or any combination thereof; and wherein each non-carbon atom or non-heteroatom substituent of R' is independently hydrogen or deuterium.

In some embodiments of Formula (II-I), one instance of X is deuterium. In some embodiments, two instances of X are deuterium. In some embodiments, at least two instances of X are deuterium. In some embodiments, all instances of X are deuterium.

In some embodiments of Formula (II-I), all instances of R are hydrogen (H). In some embodiments, at least one instance of R is H. In some embodiments, at least two instances of R are H. In some embodiments, at least three instances of R are H. In some embodiments, at least four instances of R are H. In some embodiments, at least five instances of R are H. In some embodiments, at least six instances of R are H. In some embodiments, at least seven instances of R are H. In some embodiments, at least eight instances of R are H. In some embodiments, at least nine instances of R are H. In some embodiments, at least ten instances of R are H. In some embodiments, at least eleven instances of R are H. In some embodiments, at least twelve instances of R are H. In some embodiments, at least thirteen instances of R are H. In some embodiments, at least fourteen instances of R are H. In some embodiments, at least fifteen instances of R are H. In some embodiments, at least sixteen instances of R are H. In some embodiments, at least seventeen instances of R are H. In some embodiments, at least eighteen instances of R are H. In some embodiments, at least nineteen instances of R are H. In some embodiments, at least twenty instances of R are H. In some embodiments, at least twenty-one instances of R are H. In some embodiments, at least twenty-two instances of R are H. In some embodiments, at least twenty-three instances of R are H. In some embodiments, at least twenty-four instances of R are H. In some embodiments, at least twenty-five instances of R are H. In some embodiments, at least twenty-six instances of R are H.

In some embodiments of Formula (II-I), at least one instance of R is deuterium. In some embodiments, two to ten instances of R are deuterium. In some embodiments, up to fifteen instances of R are deuterium. In some embodiments, up to twenty instances of R are deuterium. In some embodiments, all instances of R are deuterium.

In some embodiments, two instances of R are deuterium. In some embodiments, three instances of R are deuterium. In some embodiments, four instances of R are deuterium. In some embodiments, five instances of R are deuterium. In some embodiments, six instances of R are deuterium. In some embodiments, seven instances of R are deuterium. In some embodiments, eight instances of R are deuterium. In some embodiments, nine instances of R are deuterium. In some embodiments, ten instances of R are deuterium. In some embodiments, eleven instances of R are deuterium. In some embodiments, twelve instances of R are deuterium. In some embodiments, thirteen instances of R are deuterium. In some embodiments, fourteen instances of R are deuterium. In some embodiments, fifteen instances of R are deuterium. In some embodiments, sixteen instances of R are deuterium. In some embodiments, seventeen instances of R are deuterium. In some embodiments, eighteen instances of R are deuterium. In some embodiments, nineteen instances of R are deuterium. In some embodiments, twenty instances of R are deuterium. In some embodiments, twenty-one instances of R are deuterium. In some embodiments, twenty-two instances of R are deuterium. In some embodiments, twenty-three instances of R are deuterium. In some embodiments, twenty-four instances of R are deuterium. In some embodiments, twenty-five instances of R are deuterium. In some embodiments, twenty-six instances of R are deuterium.

In certain embodiments, the ester of Formula (II-I) is a caproate, cypionate, decanoate, enanthate, isobutyrate, isocaproate, phenylpropionate, propionate, or undecenoate ester. In some embodiments, the ester of Formula (II-I) is a cyclohexylpropionate, acetate, enantate benzylic acid hydrzone, furoate, hexahydrobenzoate, hexahydrobenzylcarbonate, hexahydrophenylpropionate, ketolaurate, nicotinate, phenylacetate, phosphate, undecylenate, or valerate ester. In certain embodiments, the ester of Formula (II-I) is a buciclate, benzoate, butyrate, formate, isovalerate, palmitate, phenylbutyrate, or stearate ester. In some embodiments, the compound of Formula (II-I) is not a propionate ester.

In certain embodiments, Formula (II-I) is selected from the group consisting of:

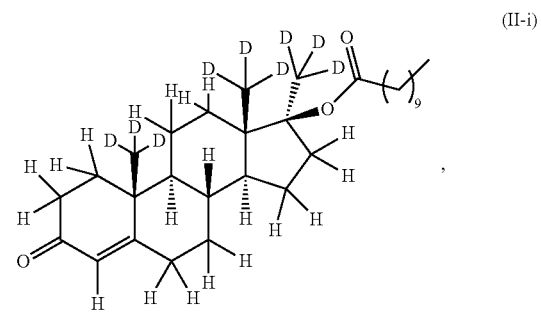
(II-i)

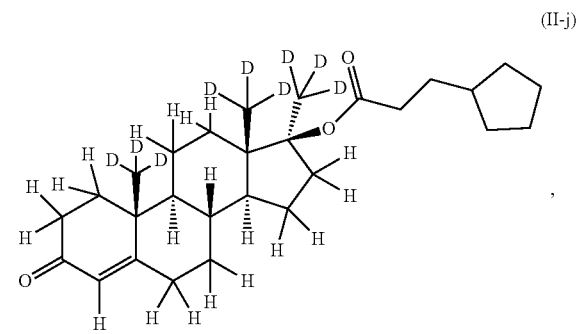
(II-j)

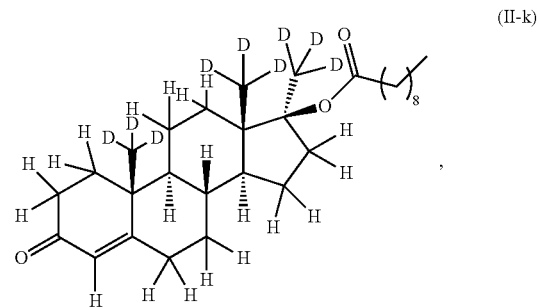
(II-k)

-continued

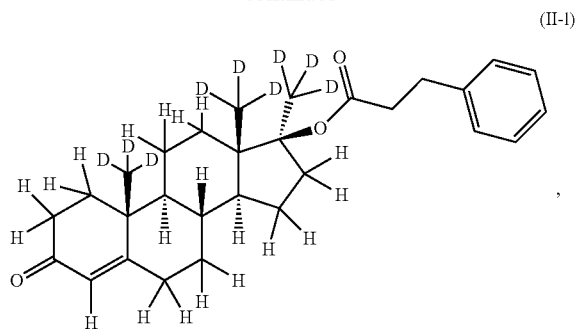

(II-l)

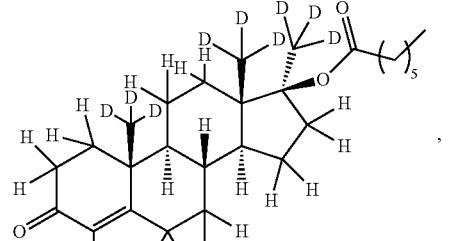

(II-m)

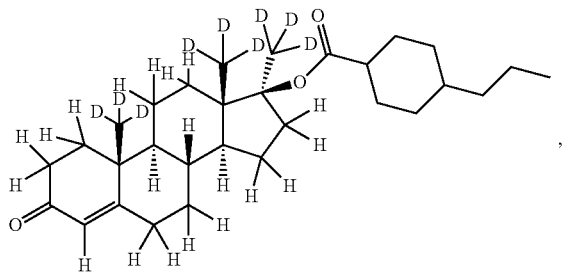

(II-n)

(II-o)

(II-p)

-continued

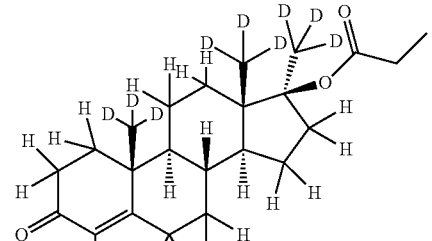

(II-q)

(II-r)

or a pharmaceutically acceptable salt, biologically active metabolite, solvate, hydrate, ester, prodrug, enantiomer, or stereoisomer thereof.

In another aspect, provided herein is a compound of Formula (II-J):

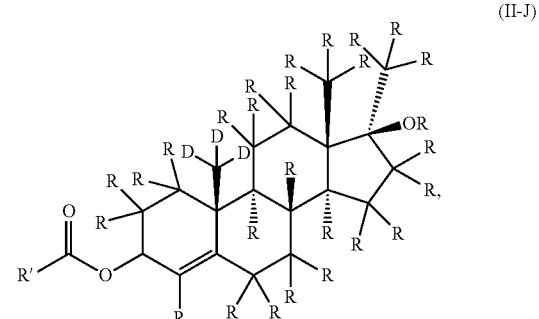

(II-J)

or a pharmaceutically acceptable salt, biologically active metabolite, solvate, hydrate, ester, prodrug, enantiomer or stereoisomer thereof;

wherein each R is independently hydrogen or deuterium;

wherein each X is independently hydrogen or deuterium;

wherein at least one instance of X is deuterium;

wherein R' is $C_{1-20}$ branched or unbranched aliphatic, branched or unbranched heteroaliphatic, carbocyclic, heterocyclic, aromatic, heteroaromatic, or any combination thereof; and wherein each non-carbon atom or non-heteroatom substituent of R' is independently hydrogen or deuterium.

In another aspect, provided herein is a compound of Formula (II-K):

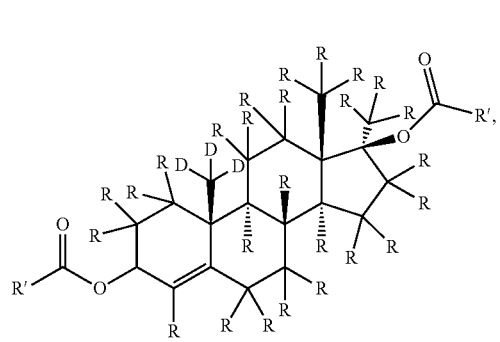

(II-K)

or a pharmaceutically acceptable salt, biologically active metabolite, solvate, hydrate, ester, prodrug, enantiomer or stereoisomer thereof;

wherein each R is independently hydrogen or deuterium;

wherein each X is independently hydrogen or deuterium;

wherein at least one instance of X is deuterium;

wherein each instance of R' is independently $C_{1-20}$ branched or unbranched aliphatic, branched or unbranched heteroaliphatic, carbocyclic, heterocyclic, aromatic, heteroaromatic, or any combination thereof; and wherein each non-carbon atom or non-heteroatom substituent of each instance of R' is independently hydrogen or deuterium.

In certain embodiments of Formulae (II-I), (II-J), and (II-K), R' is $C_{1-20}$ branched or unbranched aliphatic, branched or unbranched heteroaliphatic, carbocyclic, heterocyclic, aromatic, heteroaromatic, or any combination thereof. In certain embodiments, R' is $C_{1-20}$ branched or unbranched aliphatic, carbocyclic, aromatic, or any combination thereof. In certain embodiments, R' is $C_{1-20}$ branched or unbranched heteroaliphatic, heterocyclic, heteroaromatic, or any combination thereof. In certain embodiments, R' comprises $C_{1-20}$ branched or unbranched aliphatic. In certain embodiments, R' comprises $C_{1-20}$ branched aliphatic. In certain embodiments, R' comprises $C_{1-20}$ unbranched aliphatic. In certain embodiments, R' comprises $C_{1-20}$ branched or unbranched alkyl. In certain embodiments, R' comprises $C_{1-10}$ branched or unbranched alkyl. In certain embodiments, R' comprises $C_{1-20}$ branched or unbranched heteroaliphatic. In certain embodiments, R' comprises $C_{1-20}$ carbocyclic. In certain embodiments, R' comprises $C_{1-10}$ carbocyclic. In certain embodiments, R' comprises $C_{1-7}$ carbocyclic. In certain embodiments, R' comprises $C_{1-20}$ heterocyclic. In certain embodiments, R' comprises $C_{1-20}$ aromatic. In certain embodiments, R' comprises $C_{1-10}$ aromatic. In certain embodiments, R' comprises $C_{1-20}$ heteroaromatic. In certain embodiments, R' is methyl, ethyl, propyl, or butyl. In certain embodiments, R' is cyclopropyl, cyclobutyl, cyclopentyl, cyclohexyl, or cycloheptyl.

In another aspect, provided herein is a compound of Formula (III):

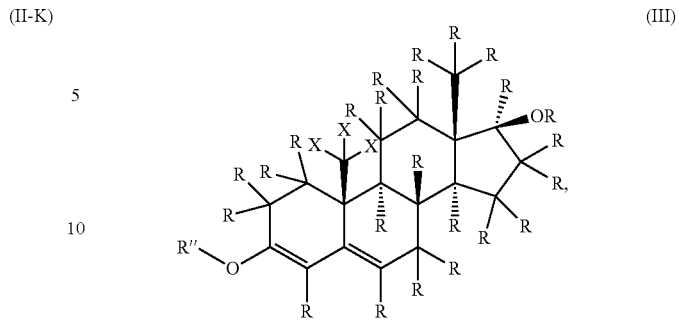

(III)

or a pharmaceutically acceptable salt, biologically active metabolite, solvate, hydrate, ester, prodrug, enantiomer or stereoisomer thereof, wherein each R is independently hydrogen or deuterium;

each X is independently hydrogen or deuterium;

R" is $C_{1-20}$ branched or unbranched aliphatic, branched or unbranched heteroaliphatic, carbocyclic, heterocyclic, aromatic, heteroaromatic, or any combination thereof; and each non-carbon atom or non-heteroatom substituent of R" is independently hydrogen or deuterium.

In another aspect, provided herein is a compound of Formula (IV):

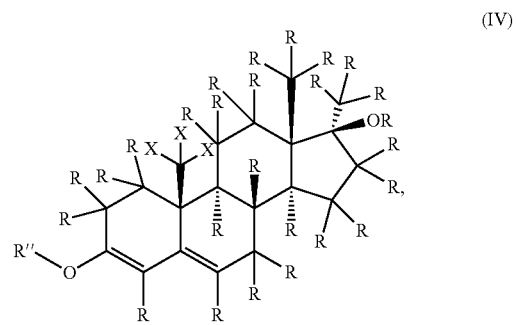

(IV)

or a pharmaceutically acceptable salt, biologically active metabolite, solvate, hydrate, ester, prodrug, enantiomer or stereoisomer wherein each R is independently hydrogen or deuterium;

each X is independently hydrogen or deuterium;

R" is $C_{1-20}$ branched or unbranched aliphatic, branched or unbranched heteroaliphatic, carbocyclic, heterocyclic, aromatic, heteroaromatic, or any combination thereof; and each non-carbon atom or non-heteroatom substituent of R" is independently hydrogen or deuterium.

In certain embodiments, R" is $C_{1-20}$ branched or unbranched aliphatic, branched or unbranched heteroaliphatic, carbocyclic, heterocyclic, aromatic, heteroaromatic, or any combination thereof. In some embodiments, R" is $C_{1-20}$ branched or unbranched aliphatic, carbocyclic, aromatic, or any combination thereof. In certain embodiments, R" is $C_{1-20}$ branched or unbranched heteroaliphatic, heterocyclic, heteroaromatic, or any combination thereof. In some embodiments, R" is comprises $C_{1-20}$ branched or unbranched aliphatic. In certain embodiments, R" comprises $C_{1-20}$ branched aliphatic. In some embodiments, R" comprises $C_{1-20}$ unbranched aliphatic. In certain embodiments, R" comprises $C_{1-20}$ branched or unbranched alkyl. In certain embodiments, R" comprises $C_{1-10}$ branched or unbranched alkyl. In certain embodiments, R" comprises $C_{1-20}$ branched or unbranched heteroaliphatic. In some embodiments, R" comprises $C_{1-20}$ carbocyclic. In certain embodiments, R" comprises $C_{1-10}$ carbocyclic. In certain embodiments, R" comprises $C_{1-7}$ carbocyclic. In certain embodiments, R" comprises $C_{1-20}$ heterocyclic. In some embodiments, R" comprises $C_{1-20}$ aromatic. In some embodiments, R" comprises $C_{1-10}$ aromatic. In certain embodiments, R" comprises $C_{1-20}$ heteroaromatic. In some embodiments, R" is methyl, ethyl, propyl, or butyl. In certain embodiments, R" is cyclopropyl, cyclobutyl, cyclopentyl, cyclohexyl, or cycloheptyl.

In some embodiments, each non-carbon atom or non-heteroatom substituent of R" is hydrogen. In some embodiments, each non-carbon atom or non-heteroatom substituent of R" is deuterium. In some embodiments, each non-carbon atom or non-heteroatom substituent of R" is deuterium, and each instance of R, X, and $R^1$ if present are hydrogen. In some embodiments, at least one non-carbon atom or non-heteroatom substituent of R" is deuterium, and each instance of R, X, and $R^1$ if present are hydrogen.

The compounds described herein (e.g., compounds of Formula (I), (II), (III), and (IV)) may comprise stable isotopes of carbon, nitrogen, and oxygen in amounts greater than their natural abundance. For example, one or more carbon atoms may be enriched with $^{13}C$ in an amount greater than about 1.1% (e.g., 1.2-1.5%, 1.5-2%, 2-10%, or more than 10%). Likewise, one or more oxygen atoms may be enriched with $^{18}O$ in an amount greater than about 0.24% (e.g., 0.25-0.5%, 0.5-1%, 1-2%, 2-10%, or greater than 10%).

In some embodiments, the compound of Formula (I), (II), (III), or (IV), or a pharmaceutically acceptable salt, biologically active metabolite, solvate, hydrate, ester, prodrug, enantiomer or stereoisomer thereof, has an isotopic purity of at least 50.0%, 60.0%, 70.0%, 75.0%, 80.0%, 85.0%, 90.0%, 95.0%, 97.0%, 98.0%, 99.0%, 99.5%, 99.7%, 99.8%, or 99.9%. In certain embodiments, the compound of Formula (I), (II), (III), or (IV), or a pharmaceutically acceptable salt, biologically active metabolite, solvate, hydrate, ester, prodrug, enantiomer or stereoisomer thereof, has an isotopic purity of at least 90.0%, 95.0%, 97.0%, 98.0%, 99.0%, 99.5%, 99.7%, 99.9%, or greater. In some embodiments, reference to a compound as described herein refers to a single molecule. In some embodiments, reference to a compound as described herein refers to more than a single molecule. For example, the compound of Formula (I), (II), (III), or (IV) may be present in an amount measured in micrograms, milligrams, grams, or kilograms, and as such comprises a large number of individual molecules. For such isotopically-labeled molecules, isotopic enrichment may be described as a percentage indicating the percent of isotopic atoms at a particular site on the molecule. The percentage can be referred to as the "isotopic purity" of the isotopically-labeled compound.

In certain embodiments, the compound of Formula (I), (II), (III), or (IV), or a pharmaceutically acceptable salt, biologically active metabolite, solvate, hydrate, ester, prodrug, enantiomer or stereoisomer thereof, has an isotopic purity of at least 50.0%. In certain embodiments, the compound of Formula (I), (II), (III), or (IV), or a pharmaceutically acceptable salt, biologically active metabolite, solvate, hydrate, ester, prodrug, enantiomer or stereoisomer thereof, has an isotopic purity of at least 60.0%. In certain embodiments, the compound of Formula (I), (II), (III), or (IV), or a pharmaceutically acceptable salt, biologically active metabolite, solvate, hydrate, ester, prodrug, enantiomer or stereoisomer thereof, has an isotopic purity of at least 70.0%. In certain embodiments, the compound of Formula (I), (II), (III), or (IV), or a pharmaceutically acceptable salt, biologically active metabolite, solvate, hydrate, ester, prodrug, enantiomer or stereoisomer thereof, has an isotopic purity of at least 75.0%. In certain embodiments, the compound of Formula (I), (II), (III), or (IV), or a pharmaceutically acceptable salt, biologically active metabolite, solvate, hydrate, ester, prodrug, enantiomer or stereoisomer thereof, has an isotopic purity of at least 80.0%. In certain embodiments, the compound of Formula (I), (II), (III), or (IV), or a pharmaceutically acceptable salt, biologically active metabolite, solvate, hydrate, ester, prodrug, enantiomer or stereoisomer thereof, has an isotopic purity of at least 85.0%. In certain embodiments, the compound of Formula (I), (II), (III), or (IV), or a pharmaceutically acceptable salt, biologically active metabolite, solvate, hydrate, ester, prodrug, enantiomer or stereoisomer thereof, has an isotopic purity of at least 90.0%. In certain embodiments, the compound of Formula (I), (II), (III), or (IV), or a pharmaceutically acceptable salt, biologically active metabolite, solvate, hydrate, ester, prodrug, enantiomer or stereoisomer thereof, has an isotopic purity of at least 95.0%. In certain embodiments, the compound of Formula (I), (II), (III), or (IV), or a pharmaceutically acceptable salt or prodrug, has an isotopic purity of at least 97.0%. In certain embodiments, the compound of Formula (I), (II), (III), or (IV), or a pharmaceutically acceptable salt, biologically active metabolite, solvate, hydrate, ester, prodrug, enantiomer or stereoisomer thereof, has an isotopic purity of at least 98.0%. In certain embodiments, the compound of Formula (I), (II), (III), or (IV), or a pharmaceutically acceptable salt, biologically active metabolite, solvate, hydrate, ester, prodrug, enantiomer or stereoisomer thereof, has an isotopic purity of at least 99.0%. In certain embodiments, the compound of Formula (I), (II), (III), or (IV), or a pharmaceutically acceptable salt, biologically active metabolite, solvate, hydrate, ester, prodrug, enantiomer or stereoisomer thereof, has an isotopic purity of at least 99.5%. In certain embodiments, the compound of Formula (I), (II), (III), or (IV), or a pharmaceutically acceptable salt, biologically active metabolite, solvate, hydrate, ester, prodrug, enantiomer or stereoisomer thereof, has an isotopic purity of at least 99.7%. In certain embodiments, the compound of Formula (I), (II), (III), or (IV), or a pharmaceutically acceptable salt, biologically active metabolite, solvate, hydrate, ester, prodrug, enantiomer or stereoisomer thereof, has an isotopic purity of at least 99.9%.

Compositions

In another aspect, provided herein is a composition comprising an effective amount (e.g., a therapeutically effective amount) of a compound described herein.

In certain embodiments, provided herein is a pharmaceutical composition comprising an effective amount of a compound of Formula (I), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formula (I-A), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formula (I-B), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formula (I-C), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formula (I-D), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formula (I-E), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formula (I-F), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formula (I-G), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formula (I-H), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formula (I-I), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formula (I-J), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formula (I-K), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formula (I-L), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formula (I-M), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formula (I-N), or a pharmaceutically acceptable salt, biologically active metabolite, solvate, hydrate, ester, prodrug, enantiomer or stereoisomer thereof.

In certain embodiments, provided herein is a pharmaceutical composition comprising an effective amount of a compound of Formulae (II), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formulae (II-A), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formulae (II-B), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formulae (II-C), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formulae (II-D), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formulae (II-E), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formulae (II-F), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formulae (II-G), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formulae (II-H), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formulae (II-I), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formulae (II-J), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of a compound of Formulae (II-K), or a pharmaceutically acceptable salt, biologically active metabolite, solvate, hydrate, ester, prodrug, enantiomer or stereoisomer thereof.

In certain embodiments, provided herein is a pharmaceutical composition comprising an effective amount of a compound of Formulae (III), or a pharmaceutically acceptable salt, biologically active metabolite, solvate, hydrate, ester, prodrug, enantiomer or stereoisomer thereof.

In certain embodiments, provided herein is a pharmaceutical composition comprising an effective amount of a compound of Formulae (IV), or a pharmaceutically acceptable salt, biologically active metabolite, solvate, hydrate, ester, prodrug, enantiomer or stereoisomer thereof.

In certain embodiments, provided herein is a pharmaceutical composition comprising an effective amount of the compound (I-a), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of the compound (I-b), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of the compound (I-c), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of the compound (I-d), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of the compound (I-e), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of the compound (I-f), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of the compound (I-g), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of the compound (I-h), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of the compound (I-i), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of the compound (I-j), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of the compound (I-k), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of the compound (I-l), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of the compound (I-m), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of the compound (I-n), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of the compound (I-o), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of the compound (I-p), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of the compound (I-q), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of the compound (I-r), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of the compound (I-s), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of the compound (I-t), or a pharmaceutically acceptable salt, biologically active metabolite, solvate, hydrate, ester, prodrug, enantiomer or stereoisomer thereof. In certain embodiments, provided herein is a pharmaceutical composition comprising an effective amount of the compound (I-u), or a pharmaceutically acceptable salt, biologically active metabolite, solvate, hydrate, ester, prodrug, enantiomer or stereoisomer thereof.

The pharmaceutical compositions described herein may comprise about 10 μg to about 1,000 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 10 μg to about 800 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 10 μg to about 600 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 10 μg to about 400 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 10 μg to about 300 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 10 μg to about 250 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 10 μg to about 200 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 10 μg to about 125 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 10 μg to about 50 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 10 μg to about 10 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 10 µg to about 5 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 25 µg to about 1,000 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 25 µg to about 800 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 25 µg to about 600 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 25 µg to about 400 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 25 µg to about 300 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 25 µg to about 250 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 25 µg to about 200 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 25 µg to about 125 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 25 µg to about 50 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 25 µg to about 10 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 25 µg to about 5 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 1 mg to about 1,000 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 1 mg to about 500 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 1 mg to about 400 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 1 mg to about 350 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 1 mg to about 300 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 1 mg to about 250 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 1 mg to about 200 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 1 mg to about 100 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 1 mg to about 75 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 1 mg to about 50 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 1 mg to about 25 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 1 mg to about 20 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 1 mg to about 15 mg of the compound of Formula (I), (II), (III), or (IV), or a pharmaceutically acceptable salt, biologically active metabolite, solvate, hydrate, ester, prodrug, enantiomer or stereoisomer thereof. In some embodiments, the composition comprises about 1 mg to about 10 mg of the compound of Formula (I), (II), (III), or (IV), or a pharmaceutically acceptable salt, biologically active metabolite, solvate, hydrate, ester, prodrug, enantiomer or stereoisomer thereof.

In certain embodiments, the weight percentage of the compound of Formula (I), (II), (III), or (IV), or a pharmaceutically acceptable salt, biologically active metabolite, solvate, hydrate, ester, prodrug, enantiomer or stereoisomer thereof, in the composition ranges from about 0.001% to about 100%. In certain embodiments, the weight percent ranges from 0.1% to 5% (e.g., 0.1% to 1%, 1% to 5%). In certain embodiments, the weight percentage ranges from about 5% to about 10%. In certain embodiments, the weight percentage ranges from about 5% to about 20%. In certain embodiments, the weight percentage ranges from about 10% to about 50%. In certain embodiments, the weight percentage ranges from about 20% to about 100%. In certain embodiments, the weight percentage ranges from about 20% to about 50%. In certain embodiments, the weight percentage ranges from about 25% to about 100%. In certain embodiments, the weight percentage ranges from about 25% to about 50%. In certain embodiments, the weight percentage ranges from about 30% to about 100%. In certain embodiments, the weight percentage ranges from about 30% to about 50%. In certain embodiments, the weight percentage ranges from about 35% to about 100%. In certain embodiments, the weight percentage ranges from about 35% to about 50%. In certain embodiments, the weight percentage ranges from about 40% to about 100%. In certain embodiments, the weight percentage ranges from about 40% to about 50%. In certain embodiments, the weight percentage ranges from about 50% to about 100%. In certain embodiments, the weight percentage ranges from about 50% to about 60%. In certain embodiments, the weight percentage ranges from about 60% to about 100%. In certain embodiments, the weight percentage ranges from about 60% to about 70%. In certain embodiments, the weight percentage ranges from about 70% to about 100%. In certain embodiments, the weight percentage ranges from about 70% to about 80%. In certain embodiments, the weight percentage ranges from about 80% to about 100%. In certain embodiments, the weight percentage ranges from about 80% to about 90%. In certain embodiments, the weight percentage ranges from about 90% to about 100%.

In certain embodiments, the pharmaceutical compositions described herein comprise an amount of isotopically-enriched testosterone, or a pharmaceutically acceptable salt, biologically active metabolite, solvate, hydrate, ester, prodrug, enantiomer or stereoisomer thereof, wherein the isotopically-enriched testosterone, or a pharmaceutically acceptable salt, biologically active metabolite, solvate, hydrate, ester, prodrug, enantiomer or stereoisomer thereof, comprises a greater percentage of a compound of Formula (I) than that which would occur naturally, e.g., as a result of the natural abundance of deuterium. In certain other embodiments, the pharmaceutical compositions described herein comprise an amount of isotopically-enriched methyltestosterone, or a pharmaceutically acceptable salt, biologically active metabolite, solvate, hydrate, ester, prodrug, enantiomer or stereoisomer thereof, wherein the isotopically-enriched methyltestosterone, or a pharmaceutically acceptable salt, biologically active metabolite, solvate, hydrate, ester, prodrug, enantiomer or stereoisomer thereof, comprises a greater percentage of a compound of Formula (II) than that which would occur naturally, e.g., as a result of the natural abundance of deuterium. In certain other embodiments, the pharmaceutical compositions described herein comprise an amount of isotopically-enriched methyltestosterone, or a pharmaceutically acceptable salt, biologically active metabolite, solvate, hydrate, ester, prodrug, enantiomer or stereoisomer thereof, wherein the isotopically-enriched methyltestosterone, or a pharmaceutically acceptable salt, biologically active metabolite, solvate, hydrate, ester, prodrug, enantiomer or stereoisomer thereof, comprises a greater percentage of a compound of Formula (III) than that which would occur naturally, e.g., as a result of the natural abundance of deuterium. In certain other embodiments, the pharmaceutical compositions described herein comprise an amount of isotopically-enriched methyltestosterone, or a pharmaceutically acceptable salt, biologically active metabolite, solvate, hydrate, ester, prodrug, enantiomer or stereoisomer thereof, wherein the isotopically-enriched methyltestosterone, or a pharmaceutically acceptable salt, biologically active metabolite, solvate, hydrate, ester, prodrug, enantiomer or stereoisomer thereof, comprises a greater percentage of a compound of Formula (IV) than that which would occur naturally, e.g., as a result of the natural abundance of deuterium. The natural abundance of deuterium is approximately 0.02% (0.03% by mass). For example, the percentage of a compound of Formula (I), (II), (III), or (IV) in the testosterone or testosterone derivative may be at least 0.1%, at least 0.5%, at least 1.0, at least 2.0%, at least 3.0%, at least 4.0%, at least 5.0%, at least 10.0%, at least 20.0%, at least 30.0%, at least 40.0%, at least 50.0%, at least 60.0%, at least 70.0%, at least 75.0%, at least 80.0%, at least 85.0%, at least 90.0%, at least 95.0%, at least 97.0%, at least 98.0%, at least 99.0%, at least 99.5%, at least 99.7%, at least 99.8%, at least 99.9%, or at least 100%. In some embodiments, the pharmaceutical composition may include a mixture or combination of both a compound of Formula (I), (II), (III), or (IV) and a compound of the same formula that is not isotopically enriched (e.g., contains a natural abundance of deuterium or less), In certain embodiments, the pharmaceutical composition may comprise amounts of both isotopically enriched (deuterated) and non-isotopically enriched forms of a compound of Formula (I), (II), (III), or (IV), or a pharmaceutically acceptable salt, biologically active metabolite, solvate, hydrate, ester, prodrug, enantiomer or stereoisomer thereof, to achieve the weight percentages described herein. In some embodiments, the weight percentage of the compound of Formula (I), (II), (III), or (IV), or a pharmaceutically acceptable salt, biologically active metabolite, solvate, hydrate, ester, prodrug, enantiomer or stereoisomer thereof, in the total amount (i.e., deuterated and non-deuterated) of testosterone, or pharmaceutically acceptable salt, biologically active metabolite, solvate, hydrate, ester, prodrug, enantiomer or stereoisomer thereof, present in the composition ranges from about 1% to about 100%. In certain embodiments, the weight percentage ranges from about 1% to about 99.9%. In certain embodiments, the weight percentage ranges from about 1% to about 99%. In certain embodiments, the weight percentage is at least 90%, at least 80%, at least 70%, at least 60%, or at least 50%.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit. In certain embodiments, a pharmaceutical composition described herein could be prepared according to the known method such as a method described in the general rules for preparations of the Japanese Pharmacopoeia, 16th edition, the United States Pharmacopoeia, and the European Pharmacopoeia, 9th edition. A pharmaceutical composition of the invention could be administered to patients appropriately depending on the dosage form.

An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein.

In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The pharmaceutical compositions described herein may further comprise a pharmaceutically acceptable carrier. In certain embodiments, the pharmaceutical composition as described herein may be formulated (e.g., using the same excipients in the same ratios and/or comprising the same dose strength) or administered in the same way as commercially available testosterone, testosterone prodrug, or testosterone derivative products, including but not limited to: Androderm, Androgel, Android 10, Android 25, Android 5, Aveed, Axiron, Delatestryl, Depo-Testadiol, Depo-Testosterone, Ditate-Ds, Fortesta, Jatenzo, Metandren, Methyltestosterone, Natesto, Oreton, Oreton Methyl, Striant, Testim, Testoderm, Testoderm Tts, Testopel, Testosterone, Testosterone Cypionate, Testosterone Cypionate-Estradiol Cypionate, Testosterone Enanthate, Testosterone Enanthate And Estradiol Valerate, Testosterone Propionate, Testosterone Undecanoate, Testred, Virilon, Vogelxo, Xyosted (Auto-injector). The FDA-approved labels for each of these products, as available at https://www.accessdata.fda.gov/scripts/cder/daf/, are incorporated herein by reference in their entirety, including with respect to their formulation, dosing, and administration.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.001% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

In certain embodiments, the pharmaceutical composition comprising a compound of Formula (I), (II), (III), or (IV), or a pharmaceutically acceptable salt, biologically active metabolite, solvate, hydrate, ester, prodrug, enantiomer or stereoisomer thereof, as described herein, is suitable for oral administration, topical administration (via direct administration or a transdermal delivery system), nasal administration, parenteral administration (e.g., subcutaneous or intramuscular administration), administration by injection, or administration by implantation.

In some embodiments, the pharmaceutical composition is suitable for oral administration. In some embodiments, an oral formulation comprising the compound of Formula (I), (II), (III), or (IV), or a pharmaceutically acceptable salt, biologically active metabolite, solvate, hydrate, ester, prodrug, enantiomer or stereoisomer thereof, may further comprise a pharmaceutically acceptable filler, diluent, lubricant, or other excipients commonly used in the manufacture of pharmaceutical drug products. In some embodiments, the oral formulation comprises a solution, suspension, sublingual film, softgel or liquid-filled capsule, or solid dosage formulation.

In some embodiments, the oral formulation comprises a softgel or liquid-filled capsule. In some embodiments, the softgel or liquid-filled capsule may be prepared as described in U.S. Pat. Nos. 8,241,664; 8,492,369; 8,778,916; 10,543,219; and 10,617,696, the disclosures of which are incorporated herein by reference in their entirety.

In some embodiments, the oral formulation comprises a solid dosage formulation. In some embodiments, the solid dosage formulation is a tablet, caplet, capsule, granule, powder, sachet, rapidly disintegrating tablet, or chewable. In some embodiments, the tablet is an immediate release, modified release, or extended release tablet. In some embodiments, the tablet is a sublingual or buccal tablet. In some embodiments, the sublingual or buccal tablet comprises a compound of Formula (I), (II), (III), or (IV), or a pharmaceutically acceptable salt, biologically active metabolite, solvate, hydrate, ester, prodrug, enantiomer or stereoisomer thereof, anhydrous lactose NF, carbomer 934P, hypromellose USP, magnesium stearate NF, lactose monohydrate NF, polycarbophil USP, colloidal silicon dioxide NF, starch NF and talc USP.

In some embodiments, the pharmaceutical composition is a topical formulation. In some embodiments, the topical formulation is a solution, cream, lotion, oil-based lotion, or gel. The gel may be prepared as described in U.S. Pat. Nos. 6,503,894; 8,466,136; and 7,320,968, the disclosures of which are incorporated herein by reference in their entirety. In some embodiments, the gel comprises one or more of ethanol, isopropyl alcohol, octisalate, and povidone. In some embodiments, the topical formulation is a gel comprising one or more of propylene glycol, purified water, ethanol, 2-propanol, oleic acid, carbomer 1382, triethanolamine, and butylated hydroxytoluene.

In some embodiments, the pharmaceutical composition is within or comprises a transdermal delivery system, e.g., a film or patch. The film or patch may be prepared as described in U.S. Pat. Nos. 4,849,224; 4,855,294; 4,863,970; 4,983,395; 5,152,997; and 5,164,190, the disclosures of which are incorporated herein in their entirety. In some embodiments, the patch consists of three layers: a non-removable polyester protective film (backing layer), an adhesive matrix containing the active substance, and a polyester removable protective layer (release liner). The backing layer may be made of a translucent polyethylene (LDPE) polymer. The matrix layer contains the active substance, and may further comprise a permeation enhancer (e.g., sorbitan oleate) and a pressure sensitive acrylic copolymer adhesive. The release liner may comprise two overlapped siliconised polyester film liner strips, designed to be peeled off and discarded by the patient prior to applying the patch to the skin. Each transdermal patch may be packed in a heat-sealed sachet.

In some embodiments, the pharmaceutical composition is suitable for nasal administration. In some embodiments, a nasal formulation is provided comprising a gel. In some embodiments, the nasal gel may be prepared as described in WO2012156822A1. In some embodiments, a pharmaceutical composition suitable for nasal administration is a gel comprising a compound of Formula (I), (II), (III), or (IV), or a pharmaceutically acceptable salt, biologically active metabolite, solvate, hydrate, ester, prodrug, enantiomer or stereoisomer thereof, castor oil, oleoyl polyoxylglycerides, and colloidal silicon dioxide.

In some embodiments, the pharmaceutical composition is suitable for administration by injection, e.g., subcutaneous injection or intramuscular injection. In some embodiments, a pharmaceutical composition suitable for administration by injection comprises a compound of Formula (I), (II), (III), or (IV), or a pharmaceutically acceptable salt, biologically active metabolite, solvate, hydrate, ester, prodrug, enantiomer or stereoisomer thereof, and a pharmaceutically acceptable oil, such as sesame oil, refined castor oil, or cottonseed oil. The pharmaceutical composition suitable for administration by injection may further comprise a solubility enhancer, such as benzyl benzoate. The pharmaceutical composition suitable for administration by injection may further comprise a preservative such as chlorobutanol or benzyl alcohol.

In some embodiments, the pharmaceutical composition is a pellet formulation suitable for implantation. In some embodiments, the pellet formulation is suitable for subcutaneous implantation. In some embodiments, the pellets are cylindrical. In some embodiments, the pellet formulation comprises a compound of Formula (I), (II), (III), or (IV), or a pharmaceutically acceptable salt, biologically active metabolite, solvate, hydrate, ester, prodrug, enantiomer or stereoisomer thereof in crystalline form, stearic acid, and polyvinylpyrrolidone.

As a formulation suitable for oral administration, the pharmaceutical composition may comprise at least 1 mg, 2 mg, 2.5 mg, 5 mg, 10 mg, 20 mg, 25 mg, 30 mg, 40 mg, 50 mg, 60 mg, 70 mg, 80 mg, 90 mg, 100 mg, 110 mg, 120 mg, 130 mg, 140 mg, 150 mg, 158 mg, 160 mg, 170 mg, 180 mg, 190 mg, 198 mg, 200 mg, 210 mg, 220 mg, 230 mg, 237 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, 500 mg, 600 mg, 700 mg, 800 mg, 900 mg, or 1,000 mg of a compound of Formula (I), (II), (III), or (IV), or a pharmaceutically acceptable salt, biologically active metabolite, solvate, hydrate, ester, prodrug, enantiomer or stereoisomer thereof. In some embodiments, the pharmaceutical composition for oral administration comprises between 1 mg-5 mg, 5 mg-10 mg, 10 mg-20 mg, 20 mg-30 mg, 30 mg-40 mg, 40 mg-50 mg, 50 mg-75 mg, 75 mg-100 mg, 100 mg-150 mg, 150 mg-200 mg, 200 mg-250 mg, 250 mg-300 mg, 300 mg-350 mg, 400 mg-450 mg, 450 mg-500 mg, 500 mg-600 mg, 600 mg-700 mg, 700 mg-800 mg, 800 mg-900 mg, 900 mg-1,000 mg of a compound of Formula (I), (II), (III), or (IV), or a pharmaceutically acceptable salt, biologically active metabolite, solvate, hydrate, ester, prodrug, enantiomer or stereoisomer thereof.

As a formulation for topical administration, such as a gel, the pharmaceutical composition may comprise at least 0.5 mg, 1 mg, 2 mg, 2.5 mg, 5 mg, 10 mg, 20 mg, 25 mg, 30 mg, 40 mg, 50 mg, 60 mg, 70 mg, 80 mg, 90 mg, or 100 mg of a compound of Formula (I), (II), (III), or (IV), or a pharmaceutically acceptable salt, biologically active metabolite, solvate, hydrate, ester, prodrug, enantiomer or stereoisomer thereof. In some embodiments, the pharmaceutical composition for topical administration comprises between 0.5 mg-1 mg, 1 mg-5 mg, 5 mg-10 mg, 10 mg-20 mg, 20 mg-30 mg, 30 mg-40 mg, 40 mg-50 mg, 50 mg-75 mg, 75 mg-100 mg of a compound of Formula (I), (II), (III), or (IV), or a pharmaceutically acceptable salt, biologically active metabolite, solvate, hydrate, ester, prodrug, enantiomer or stereoisomer thereof. In some embodiments, the topical formulation is a gel provided within unit dose packaging, such as a tube or packet. In some embodiments, the total weight of the product within the packaging is 0.5 grams, 1 gram, 1.25 grams, 2 grams, 2.5 grams, 5 grams, or 10 grams. In some embodiments, the topical formulation is within a metered dose pump. In some embodiments, one pump of the metered dose pump provides at least 0.5 grams, 1 gram, 1.25 grams, 2 grams, 5 grams, or 10 grams of the topical formulation.

As a transdermal delivery system, the pharmaceutical composition may be configured to provide at least 0.5 mg, 1 mg, 2 mg, 2.5 mg, 4 mg, 5 mg, 6 mg, 7 mg, 7.5 mg, 8 mg, 9 mg, or 10 mg of a compound of Formula (I), (II), (III), or (IV), or a pharmaceutically acceptable salt, biologically active metabolite, solvate, hydrate, ester, prodrug, enantiomer or stereoisomer thereof, in a 24-hour period. In some embodiments, the pharmaceutical composition may be configured to provide between 1 mg-5 mg or 5 mg-10 mg of a compound of Formula (I), (II), (III), or (IV), or a pharmaceutically acceptable salt, biologically active metabolite, solvate, hydrate, ester, prodrug, enantiomer or stereoisomer thereof, in a 24-hour period.

As a formulation for nasal administration, such as a gel, the pharmaceutical composition may comprise at least 1 mg, 2 mg, 2.5 mg, 4 mg, 5 mg, 10 mg, 11 mg, 20 mg, 25 mg, 30 mg, 33 mg, 40 mg, 50 mg, 60 mg, 70 mg, 80 mg, 90 mg, or 100 mg of a compound of Formula (I), (II), (III), or (IV), or a pharmaceutically acceptable salt, biologically active metabolite, solvate, hydrate, ester, prodrug, enantiomer or stereoisomer thereof. In some embodiments, the composition for nasal administration may comprise between 1 mg-2 mg, 2 mg-5 mg, 5 mg-10 mg, 10 mg-20 mg, 20 mg-30 mg, 30 mg-40 mg, 40 mg-50 mg, 50 mg-60 mg, 60 mg-70 mg, 70 mg-80 mg, 80 mg-90 mg, or 90 mg-100 mg of a compound of Formula (I), (II), (III), or (IV), or a pharmaceutically acceptable salt, biologically active metabolite, solvate, hydrate, ester, prodrug, enantiomer or stereoisomer thereof.

As a formulation for injection, the pharmaceutical composition may comprise at least 10 mg, 15 mg, 20 mg, 25 mg, 30 mg, 50 mg, 75 mg, 100 mg, 150 mg, 200 mg, 250 mg, 300 mg, 350 mg, 400 mg, or 500 mg per mL of a compound of Formula (I), (II), (III), or (IV), or a pharmaceutically acceptable salt, biologically active metabolite, solvate, hydrate, ester, prodrug, enantiomer or stereoisomer thereof. In some embodiments, 1 mL of the pharmaceutical composition comprises about 10-25 mg, about 25 mg-50 mg, about 50 mg-75 mg, about 75 mg-100 mg, about 100 mg-150 mg, about 150 mg-200 mg, about 200 mg-250 mg, about 250 mg-300 mg, about 300 mg-350 mg, about 350 mg-400 mg, or about 400 mg-500 mg of a compound of Formula (I), (II), (III), or (IV), or a pharmaceutically acceptable salt, biologically active metabolite, solvate, hydrate, ester, prodrug, enantiomer or stereoisomer thereof. In some embodiments, the formulation for injection may be provided within a "ready to use" product. In some embodiments, the "ready to use" product is an autoinjector.

In certain embodiments, the pharmaceutical composition is configured to deliver a low dose of a compound of Formula (I), (II), (III), or (IV), or a pharmaceutically acceptable salt, biologically active metabolite, solvate, hydrate, ester, prodrug, enantiomer or stereoisomer thereof. In some embodiments, where the formulation is a transdermal delivery formulation (e.g., a film or a patch), the pharmaceutical composition may provide 10 µg, 25 µg, 50 µg, 100 µg, 150 µg, 200 µg, 250 µg, 300 µg, 350 µg, 400 µg, or 450 µg of a compound of Formula (I), (II), (III), or (IV), or a pharmaceutically acceptable salt, biologically active metabolite, solvate, hydrate, ester, prodrug, enantiomer or stereoisomer thereof. In some embodiments, where the formulation is for oral, topical, transdermal, or parenteral administration, or for implantation, the formulation may provide a dose of the pharmaceutical composition that approximates the natural physiological testosterone concentration of healthy pre-menopausal women.

In certain embodiments of the methods and compositions described herein, the effective amount is effective in treating the disease. In certain embodiments, the effective amount is effective in preventing the disease. Pharmaceutical compositions used in connection with the methods described herein comprise an effective amount of a compound as described herein.

In some embodiments, where the pharmaceutical composition comprises a transdermal delivery system (e.g., a film or patch), the effective amount is at least 1.0 mg/day, 2.0 mg/day, 2.5 mg/day, 3 mg/day, 4 mg/day, 5 mg/day, 6 mg/day, 7 mg/day, 7.5 mg/day, 8.0 mg/day, 8.5 mg/day, 9.0 mg/day, 9.5 mg/day, or 10 mg/day.

In some embodiments, where the pharmaceutical composition comprises a gel to be administered topically, the effective amount is at least 5 mg, 10 mg, 12.5 mg, 15 mg, 20 mg, 25 mg, 30 mg, 40 mg, 50 mg, 75 mg, 100 mg, 150 mg, or 200 mg daily. In some embodiments, where the pharmaceutical composition comprises a gel to be administered nasally, the effective amount in the methods described herein is at least 5 mg, 10 mg, 12.5 mg, 15 mg, 20 mg, 25 mg, 30 mg, 33 mg, 40 mg, 50 mg, 75 mg, 100 mg, 150 mg, or 200 mg daily.

In some embodiments, where the pharmaceutical composition comprises a formulation to be injected subcutaneously or intramuscularly, the effective amount is at least 25 mg, 50 mg, 75 mg, 100 mg, 150 mg, 200 mg, 250 mg, 500 mg, or 750 mg per week, every two weeks, every four weeks, or every ten weeks.

In some embodiments, where the pharmaceutical composition comprises a formulation for oral administration, the effective amount is at least 5 mg, 10 mg, 20 mg, 25 mg, 30 mg, 40 mg, 50 mg, 100 mg, 150 mg, 200 mg, or 250 mg daily.

In certain embodiments, e.g., where a transdermal delivery system is used for treating sexual disorders in female humans, the effective amount is at least 25 µg, 50 µg, 100 µg, 150 µg, 200 µg, 250 µg, 300 µg, 350 µg, 400 µg, 450 µg, or 500 µg daily.

In some embodiments, the effective amount that is administered is 5%, 10%, 15%, 20%, 25%, 30%, 35%, 40%, 45%, 50%, 60%, 70%, 75%, or 80% less than the effective amount of the non-isotopically enriched compound of the same formula when administered by the same route of administration.

In certain embodiments, the composition is administered more frequently than a composition comprising non-isotopically enriched testosterone or methyltestosterone of the same formula via the same route of administration. In some embodiments, the composition is administered less frequently than a composition comprising non-isotopically enriched testosterone or methyltestosterone of the same formula via the same route of administration. In certain embodiments, the composition is administered for a shorter total period of administration than a composition comprising non-isotopically enriched testosterone or methyltestosterone of the same formula via the same route of administration. In some embodiments, the composition increases the duration of action of the active ingredient relative to that of a composition comprising non-isotopically enriched testosterone or methyltestosterone of the same formula via the same route of administration.

In certain embodiments, the pharmaceutical composition described herein is formulated for administration at least once daily (e.g., once daily). In certain embodiments, the pharmaceutical composition comprising a compound of Formula (I), (II), (III), or (IV), or a pharmaceutically acceptable salt, biologically active metabolite, solvate, hydrate, ester, prodrug, enantiomer or stereoisomer thereof, is formulated for administration at least twice daily (e.g., twice daily). In certain embodiments, the pharmaceutical composition described herein is configured for administration on a less frequent basis, e.g., every other day, once per week, every two weeks, every three weeks, every four weeks, monthly, every two months, every three months, every four months, or every six months.

Certain pharmaceutical compositions described herein may be configured (i.e., formulated) to achieve longer half-lives compared to non-isotopically enriched testosterone or methyltestosterone. In certain embodiments, the longer half-life is due to the nature of the compound of Formula (I), (II), (III), or (IV), or a pharmaceutically acceptable salt, biologically active metabolite, solvate, hydrate, ester, prodrug, enantiomer or stereoisomer thereof. In some embodiments, the longer half-life is due to the formulation of the composition. In certain embodiments, the longer half-life is due both to the nature (e.g., intrinsic properties)

of the compound of Formula (I), (II), (III), or (IV), or a pharmaceutically acceptable salt, biologically active metabolite, solvate, hydrate, ester, prodrug, enantiomer or stereoisomer thereof, and to the formulation of the composition.

In some embodiments, the half-life of a composition described herein is at least 5 minutes. In some embodiments, the half-life of a composition described herein is at least 10 minutes. In some embodiments, the half-life of a composition described herein is at least 30 minutes. In some embodiments, the half-life of a composition described herein is at least 1 hour. In some embodiments, the half-life of a composition described herein is at least 2 hours. In some embodiments, the half-life of a composition described herein is at least 4 hours. In some embodiments, the half-life of a composition described herein is at least 6 hours. In some embodiments, the half-life of a composition described herein is at least 12 hours. In some embodiments, the half-life of a composition described herein is at least one day. In some embodiments, the half-life of a composition described herein is at least two days. In some embodiments, the half-life of a composition described herein is at least three days. In some embodiments, the half-life of a composition described herein is at least one week. In some embodiments, the half-life of a composition described herein is at least two weeks.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof, and/or in inhibiting the activity of a protein kinase in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both. In some embodiments, the additional pharmaceutical agent achieves a desired effect for the same disorder. In some embodiments, the additional pharmaceutical agent achieves different effects.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the compound or composition described herein in a single dose or composition or administered separately in different doses or compositions. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, steroidal or non-steroidal anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, anesthetics, anti-coagulants, inhibitors of an enzyme, steroidal agents, steroidal or antihistamine, antigens, vaccines, antibodies, decongestant, sedatives, opioids, analgesics, anti-pyretics, hormones, and prostaglandins. In certain embodiments, the additional pharmaceutical agent is an anti-proliferative agent. In certain embodiments, the additional pharmaceutical agent is an anti-cancer agent. In certain embodiments, the additional pharmaceutical agent is a hormone receptor modulator (e.g., estrogen receptor modulators and androgen receptor modulators). In certain embodiments, the additional pharmaceutical agent is an aromatase inhibitor, selective estrogen receptor modulator, or selective androgen receptor modulator.

Additional pharmaceutical agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

In other embodiments, the pharmaceutical composition may comprise a compound of Formula (I), (II), (III), or (IV), or a pharmaceutically acceptable salt, biologically active metabolite, solvate, hydrate, ester, prodrug, enantiomer or stereoisomer thereof, as the sole active ingredient, or may be combined or co-administered in a pharmaceutical composition with one or more other active ingredients (i.e., one or more additional agents), to treat a number of conditions or diseases. Non-limiting examples of other active ingredients that may be combined or co-administered include: additional androgens or estrogens (e.g., estradiol); vitamins, such as vitamin E; erectile dysfunction drugs, such as sildenafil or tadalafil; gonadotropin-releasing hormone agonists; aromatase inhibitors; selective estrogen receptor modulators; or selective androgen receptor modulators.

In certain embodiments, the pharmaceutical composition comprising a compound of Formula (I), (II), (III), or (IV) may be used without the co-administration of an aromatase inhibitor. In some embodiments, the pharmaceutical composition comprising a compound of Formula (I), (II), (III), or (IV) results in reduced use of a co-administered aromatase inhibitor.

In certain embodiments, the pharmaceutical composition comprising a compound of Formula (I), (II), (III), or (IV) may be used without the co-administration of a selective estrogen receptor modulator. In some embodiments, the pharmaceutical composition comprising a compound of Formula (I), (II), (III), or (IV) results in reduced use of a co-administered selective estrogen receptor modulator.

Kits

Also encompassed by the disclosure are kits (e.g., pharmaceutical packs). In certain embodiments, the kit comprises a pharmaceutical composition described herein, and instructions for using the pharmaceutical composition. In some embodiments, the kit comprises a pharmaceutical composition or compound described herein and a first container (e.g., a vial, ampule, bottle, syringe, and/or dispenser package, or other suitable container), wherein the first container includes the pharmaceutical composition. In certain embodiments, the kit may optionally further include a second container (e.g., a vial, ampule, bottle, syringe, and/or dispenser package, or other suitable container). In some embodiments, the second container comprises a pharmaceutical excipient for dilution or suspension of a pharmaceutical composition or compound described herein. In certain embodiments, the pharmaceutical composition or compound described herein provided in the first container and the second container are combined to form one-unit dosage form. In some embodiments, the kit further comprises instructions for use, e.g., instructions for combining the container components, and/or instructions for administering the container components to a subject.

In certain embodiments, the instructions are for administering the pharmaceutical composition to a subject in need thereof. In certain embodiments, the instructions comprise information required by a regulatory agency, such as the U.S. Food and Drug Administration (FDA) or the European Agency for the Evaluation of Medicinal Products (EMA). In certain embodiments, the instructions comprise prescribing information.

Therapeutic Methods and Uses

Various factors contribute to the utility or efficacy of the disclosed compounds and compositions in the methods described herein. Such factors include the pharmacokinetics of deuterated testosterone, deuterated methyltestosterone, or derivatives thereof (e.g., a compound of Formula (I), (II), (III), or (IV)), the pharmacokinetics of non-deuterated testosterone or non-deuterated methyltestosterone, and the associated formation of DHT and estradiol. The pharmacokinetics of deuterated and non-deuterated testosterone and methyltestosterone may be affected by the route of administration and may manifest in physiological effects. Pharmacokinetics in a particular subject may also be affected by such factors as age, weight, body mass index, previous or concurrent injection or use of other pharmacologically-active substances. In certain embodiments, the metabolic profile of a deuterated testosterone compound or deuterated methyltestosterone compound is affected by the health, physical fitness, sleep quality, dietary habits, and pharmacological habits of the subject. Other factors that contribute to the utility or efficacy of the disclosed compounds and compositions relate to the cognitive or emotional health of the subject. Such factors include clinical conditions such as psychiatric or neurological disorders.

Accordingly, in certain embodiments, the deuterated testosterone, deuterated methyltestosterone, or derivatives thereof, and compositions described herein have favorable or advantageous pharmacokinetic properties. Such properties include a favorable metabolic profile, e.g., a favorable ratio of metabolite formation upon administration. In certain embodiments, the favorable metabolic profile results in a reduction of undesirable side effects.

The present disclosure also provides methods of using the compositions described herein. In another aspect, the present disclosure provides methods of delivering to a subject in need thereof a composition (e.g., pharmaceutical composition) described herein.

In another aspect, the present disclosure provides methods of administering an androgen therapy or androgen agonist to a subject in need thereof, the method comprising administering to the subject a pharmaceutical composition comprising an effective amount of a compound of the present disclosure. In some embodiments, the method of administering an androgen therapy or androgen agonist to a subject in need thereof comprises administering to the subject a pharmaceutical composition comprising an effective amount of a compound of Formula (I). In certain embodiments, the method of administering an androgen therapy to a subject in need thereof comprises administering to the subject a pharmaceutical composition comprising an effective amount of a compound of Formula (II). In certain embodiments, the method of administering an androgen therapy to a subject in need thereof comprises administering to the subject a pharmaceutical composition comprising an effective amount of a compound of Formula (III). In certain embodiments, the method of administering an androgen therapy to a subject in need thereof comprises administering to the subject a pharmaceutical composition comprising an effective amount of a compound of Formula (IV).

In another aspect, the present disclosure provides methods of treating a disease or condition in a subject in need thereof comprising administering to the subject in need thereof an effective amount (e.g., a therapeutically effective amount) of a compound or composition (e.g., pharmaceutical composition) of the present disclosure.

In another aspect, the present disclosure provides methods of preventing a disease or condition in a subject in need thereof comprising administering to the subject in need thereof an effective amount (e.g., a prophylactically effective amount) of a compound or composition (e.g., pharmaceutical composition) of the present disclosure.

In another aspect, the present disclosure provides methods of treating or preventing a disease that is responsive to an androgen agonist therapy in a subject in need thereof, while avoiding one or more side effects associated with the administration of non-isotopically enriched testosterone, the method comprising administering to the subject an effective amount (e.g., a therapeutically effective amount or a prophylactically effective amount) of a compound or composition (e.g., a pharmaceutical composition) of the present disclosure.

In another aspect, provided herein are uses of the compounds or compositions of the present disclosure in the manufacture of a medicament for treating a disease or condition.

In another aspect, provided herein are uses of the compounds or compositions of the present disclosure for treating or preventing a disease or condition in a subject.

In any of the methods described herein, the composition may comprise a compound of Formula (I), (II), (III), or (IV), or a pharmaceutically acceptable salt, biologically active metabolite, solvate, hydrate, ester, prodrug, enantiomer or stereoisomer thereof. In certain embodiments, the compound of Formula (I) is a compound of Formula (I-a), (I-b), (I-c), (I-d), (I-e), (I-f), (I-g), (I-h), (I-if), (I-j), or (I-k), or a pharmaceutically acceptable salt, biologically active metabolite, solvate, hydrate, ester, prodrug, enantiomer or stereoisomer thereof. In some embodiments, the compound of Formula (I) is a compound of Formula (I-a), (I-b), (I-c), or (I-d), or a pharmaceutically acceptable salt, biologically active metabolite, solvate, hydrate, ester, prodrug, enantiomer or stereoisomer thereof. In certain embodiments, the compound of Formula (I) is a compound of Formula (I-a), (I-b), or (I-c), or a pharmaceutically acceptable salt, biologically active metabolite, solvate, hydrate, ester, prodrug, enantiomer or stereoisomer thereof. In certain embodiments the compound of Formula (II) is a compound of Formula (II-a), (II-b), (II-c), (II-d), (II-e), (II-f), (II-g), (II-h), (II-i), (II-j), (II-k), (II-l), (II-m), (II-n), (II-o), (II-p), (II-q), or (II-r), or a pharmaceutically acceptable salt, biologically active metabolite, solvate, hydrate, ester, prodrug, enantiomer or stereoisomer thereof. In some embodiments, the compound of Formula (II) is a compound of Formula (II-a), (II-b), (II-c), or (II-d).

In certain embodiments, the subject is an animal. In certain embodiments, the animal may be of either sex and may be at any stage of development. In certain embodiments, the subject described herein is a human. In certain embodiments, the human may be an infant, an adolescent, an adult, or an elderly adult. As used herein, the term "infant" refers to a human having an age of up to 24 months. The term "adolescent" as used herein refers to a human having an age of 24 months to 18 years. In certain embodiments, the subject is an adolescent having an age of 12 years to 18 years. The term "adult" as used herein refers to a human having an age of 18 years to 65 years. The term "elderly adult" as used herein refers to a human having an age of greater than 65 years. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a dog. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice, transgenic pigs). In certain embodiments, a subject in need thereof is a subject in need of delivery of an active agent or a composition, a subject in need of treatment of a disease, or a subject in need of prevention of a disease. In certain embodiments, a subject is resistant to an aromatase inhibitor, a selective estrogen receptor modulator, a selective estrogen receptor degrader, or a selective androgen receptor modulator.

In certain embodiments, the subject is a male or female human. In certain embodiments, the subject is a male human. In certain embodiments, the subject is a female human. In certain embodiments, the subject is a premenopausal or postmenopausal female. In certain embodiments, the subject is a premenopausal female. In certain embodiments, the subject is a postmenopausal female. In certain embodiments, the method comprises determining the level of testosterone in the premenopausal or postmenopausal female prior to administering the pharmaceutical composition. In certain embodiments, the method comprises determining the level of testosterone in the premenopausal female prior to administering the pharmaceutical composition. In certain embodiments, the method comprises determining the level of testosterone in the postmenopausal female prior to administering the pharmaceutical composition. In certain embodiments, the subject is a postmenopausal female, and the method comprises administering a dose configured to achieve a level of testosterone comparable or equivalent to the physiological testosterone concentration in the subject when premenopausal, or to an average physiological testosterone concentration in premenopausal female (which average may take into account age, race, weight, and ethnicity).

In certain embodiments, the diseases or conditions are responsive to an androgen receptor agonist. In certain embodiments, the disease or conditions are selected from hypogonadism (primary and hypogonadotropic), whether congenital or acquired; constitutional delay of growth and puberty in adolescent boys; weight loss in AIDS patients with HIV-associated wasting; vulvar dystrophies; micropenis; breast cancer, including advancing inoperable metastatic (skeletal) mammary cancer in female humans who are 1 to 5 years postmenopausal; and sexual disorders.

In some embodiments, a method is provided for treating hypogonadism in a subject in need thereof, the method comprising administering to the subject a pharmaceutical composition comprising an effective amount of a compound of a formula disclosed herein, or a pharmaceutically acceptable salt, biologically active metabolite, solvate, hydrate, ester, prodrug, enantiomer or stereoisomer thereof. In some embodiments, the hypogonadism is primary hypogonadism or hypogonadotropic hypogonadism. In some embodiments, the hypogonadism is primary hypogonadism. In some embodiments, the hypogonadism is hypogonadotropic hypogonadism. In some embodiments, the hypogonadotropic hypogonadism is isolated hypogonadotropic hypogonadism or Kallman syndrome. In some embodiments, the hypogonadism is not hypogonadotropic hypogonadism. In some embodiments, the hypogonadism is congenital. In some embodiments, the hypogonadism is acquired.

In certain embodiments of the method of treating hypogonadism, the compound is of Formula (I). In certain embodiments, the compound is of Formula (I-A). In certain embodiments, the compound is of Formula (I-B). In certain embodiments, the compound is of Formula (I-C). In certain embodiments, the compound is of Formula (I-D). In certain embodiments, the compound is of Formula (I-E). In certain embodiments, the compound is of Formula (I-F). In certain embodiments, the compound is of Formula (I-G). In certain embodiments, the compound is of Formula (I-H). In certain embodiments, the compound is of Formula (I-I). In certain embodiments, the compound is of Formula (I-J). In certain embodiments, the compound is of Formula (I-K). In certain embodiments, the compound is of Formula (I-L). In certain embodiments, the compound is of Formula (I-M). In certain embodiments, the compound is of Formula (I-N).

In certain embodiments of the method of treating hypogonadism, the compound is Formula (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), (I-s), (I-t), (I-u), or a pharmaceutically acceptable salt, biologically active metabolite, solvate, hydrate, ester, prodrug, enantiomer or stereoisomer thereof.

In certain embodiments of the method of treating hypogonadism, the compound is of Formula (II). In certain embodiments, the compound is of Formula (II-A). In certain embodiments, the compound is of Formula (II-B). In certain embodiments, the compound is of Formula (II-C). In certain embodiments, the compound is of Formula (II-D). In certain embodiments, the compound is of Formula (II-E). In certain embodiments, the compound is of Formula (II-F). In certain embodiments, the compound is of Formula (II-G). In certain embodiments, the compound is of Formula (II-H). In certain embodiments, the compound is of Formula (II-I). In certain embodiments, the compound is of Formula (II-J). In certain embodiments, the compound is of Formula (II-K).

In certain embodiments of the method of treating hypogonadism, the compound is Formula (II-a), (II-b), (II-c), (II-d), (II-e), (II-f), (II-g), (II-h), (II-i), (II-j), (II-k), (II-l), (II-m), (II-n), (II-o), (II-p), (II-q), or (II-r), or a pharmaceutically acceptable salt, biologically active metabolite, solvate, hydrate, ester, prodrug, enantiomer or stereoisomer thereof.

In certain embodiments of the method of treating hypogonadism, the compound is of Formula (III). In some embodiments of the method of treating hypogonadism, the compound is of Formula (IV).

In some embodiments, the method for treating hypogonadism reduces side effects associated with the administration of non-isotopically enriched testosterone or methyltestosterone.

In some embodiments, a method is provided for treating constitutional delay of growth and puberty in adolescent boys in need thereof, the method comprising administering to the subject a pharmaceutical composition comprising an effective amount of a compound of a formula disclosed herein, or a pharmaceutically acceptable salt, biologically active metabolite, solvate, hydrate, ester, prodrug, enantiomer or stereoisomer thereof.

In certain embodiments of the method of treating constitutional delay of growth and puberty in adolescent boys, the compound is of Formula (I). In certain embodiments, the compound is of Formula (I-A). In certain embodiments, the compound is of Formula (I-B). In certain embodiments, the compound is of Formula (I-C). In certain embodiments, the compound is of Formula (I-D). In certain embodiments, the compound is of Formula (I-E). In certain embodiments, the compound is of Formula (I-F). In certain embodiments, the compound is of Formula (I-G). In certain embodiments, the compound is of Formula (I-H). In certain embodiments, the compound is of Formula (I-I). In certain embodiments, the compound is of Formula (I-J). In certain embodiments, the compound is of Formula (I-K). In certain embodiments, the compound is of Formula (I-L). In certain embodiments, the compound is of Formula (I-M). In certain embodiments, the compound is of Formula (I-N).

In certain embodiments of the method of treating constitutional delay of growth and puberty in adolescent boys, the compound is Formula (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), (I-s), (I-t), (I-u), or a pharmaceutically acceptable salt, biologically active metabolite, solvate, hydrate, ester, prodrug, enantiomer or stereoisomer thereof.

In certain embodiments of the method of treating constitutional delay of growth and puberty in adolescent boys, the compound is of Formula (II). In certain embodiments, the compound is of Formula (II-A). In certain embodiments, the compound is of Formula (II-B). In certain embodiments, the compound is of Formula (II-C). In certain embodiments, the compound is of Formula (II-D). In certain embodiments, the compound is of Formula (II-E). In certain embodiments, the compound is of Formula (II-F). In certain embodiments, the compound is of Formula (II-G). In certain embodiments, the compound is of Formula (II-H). In certain embodiments, the compound is of Formula (II-I). In certain embodiments, the compound is of Formula (II-J). In certain embodiments, the compound is of Formula (II-K).

In certain embodiments of the method of treating constitutional delay of growth and puberty in adolescent boys, the compound is Formula (II-a), (II-b), (II-c), (II-d), (II-e), (II-f), (II-g), (II-h), (II-i), (II-j), (II-k), (II-l), (II-m), (II-n), (II-o), (II-p), (II-q), or (II-r), or a pharmaceutically acceptable salt, biologically active metabolite, solvate, hydrate, ester, prodrug, enantiomer or stereoisomer thereof.

In certain embodiments of the method of treating constitutional delay of growth and puberty in adolescent boys, the compound is of Formula (III). In some embodiments of the method of treating constitutional delay of growth and puberty in adolescent boys, the compound is of Formula (IV).

In some embodiments, the method for treating constitutional delay of growth and puberty in adolescent boys reduces side effects associated with the administration of non-isotopically enriched testosterone or methyltestosterone.

In some embodiments, a method is provided for treating weight loss associated with HW-associated wasting in a subject in need thereof, the method comprising administering to the subject a pharmaceutical composition comprising an effective amount of a compound of a formula disclosed herein, or a pharmaceutically acceptable salt, biologically active metabolite, solvate, hydrate, ester, prodrug, enantiomer or stereoisomer thereof.

In certain embodiments of the method of treating weight loss associated with HIV-associated wasting, the compound is of Formula (I). In certain embodiments, the compound is of Formula (I-A). In certain embodiments, the compound is of Formula (I-B). In certain embodiments, the compound is of Formula (I-C). In certain embodiments, the compound is of Formula (I-D). In certain embodiments, the compound is of Formula (I-E). In certain embodiments, the compound is of Formula (I-F). In certain embodiments, the compound is of Formula (I-G). In certain embodiments, the compound is of Formula (I-H). In certain embodiments, the compound is of Formula (I-I). In certain embodiments, the compound is of Formula (I-J). In certain embodiments, the compound is of Formula (I-K). In certain embodiments, the compound is of Formula (I-L). In certain embodiments, the compound is of Formula (I-M). In certain embodiments, the compound is of Formula (I-N).

In certain embodiments of the method of treating weight loss associated with HIV-associated wasting, the compound is Formula (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), (I-s), (I-t), (I-u), or a pharmaceutically acceptable salt, biologically active metabolite, solvate, hydrate, ester, prodrug, enantiomer or stereoisomer thereof.

In certain embodiments of the method of treating weight loss associated with HIV-associated wasting, the compound is of Formula (II). In certain embodiments, the compound is of Formula (II-A). In certain embodiments, the compound is of Formula (II-B). In certain embodiments, the compound is of Formula (II-C). In certain embodiments, the compound is of Formula (II-D). In certain embodiments, the compound is of Formula (II-E). In certain embodiments, the compound is of Formula (II-F). In certain embodiments, the compound is of Formula (II-G). In certain embodiments, the compound is of Formula (II-H). In certain embodiments, the compound is of Formula (II-I). In certain embodiments, the compound is of Formula (II-J). In certain embodiments, the compound is of Formula (II-K).

In certain embodiments of the method of treating weight loss associated with HIV-associated wasting, the compound is Formula (II-a), (II-b), (II-c), (II-d), (II-e), (II-f), (II-g), (II-h), (II-i), (II-j), (II-k), (II-l), (II-m), (II-n), (II-o), (II-p), (II-q), or (II-r), or a pharmaceutically acceptable salt, biologically active metabolite, solvate, hydrate, ester, prodrug, enantiomer or stereoisomer thereof.

In certain embodiments of the method of treating weight loss associated with HIV-associated wasting, the compound is of Formula (III). In some embodiments of the method of treating weight loss associated with HIV-associated wasting, the compound is of Formula (IV).

In some embodiments, the method for treating weight loss associated with HIV-associated wasting reduces side effects associated with the administration of non-isotopically enriched testosterone or methyltestosterone.

In some embodiments, a method is provided for treating micropenis in a subject in need thereof, the method comprising administering to the subject a pharmaceutical composition comprising an effective amount of a compound of a formula disclosed herein, or a pharmaceutically acceptable salt, biologically active metabolite, solvate, hydrate, ester, prodrug, enantiomer or stereoisomer thereof.

In certain embodiments of the method of treating micropenis, the compound is of Formula (I). In certain embodiments, the compound is of Formula (I-A). In certain embodiments, the compound is of Formula (I-B). In certain embodiments, the compound is of Formula (I-C). In certain embodiments, the compound is of Formula (I-D). In certain embodiments, the compound is of Formula (I-E). In certain embodiments, the compound is of Formula (I-F). In certain embodiments, the compound is of Formula (I-G). In certain embodiments, the compound is of Formula (I-H). In certain embodiments, the compound is of Formula (I-I). In certain embodiments, the compound is of Formula (I-J). In certain embodiments, the compound is of Formula (I-K). In certain embodiments, the compound is of Formula (I-L). In certain embodiments, the compound is of Formula (I-M). In certain embodiments, the compound is of Formula (I-N).

In certain embodiments of the method of treating micropenis, the compound is Formula (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), (I-s), (I-t), (I-u), or a pharmaceutically acceptable salt, biologically active metabolite, solvate, hydrate, ester, prodrug, enantiomer or stereoisomer thereof.

In certain embodiments of the method of treating micropenis, the compound is of Formula (II). In certain embodiments, the compound is of Formula (II-A). In certain embodiments, the compound is of Formula (II-B). In certain embodiments, the compound is of Formula (II-C). In certain embodiments, the compound is of Formula (II-D). In certain embodiments, the compound is of Formula (II-E). In certain embodiments, the compound is of Formula (II-F). In certain embodiments, the compound is of Formula (II-G). In certain embodiments, the compound is of Formula (II-H). In certain embodiments, the compound is of Formula (II-I). In certain embodiments, the compound is of Formula (II-J). In certain embodiments, the compound is of Formula (II-K).

In certain embodiments of the method of treating micropenis, the compound is Formula (II-a), (II-b), (II-c), (II-d), (II-e), (II-f), (II-g), (II-h), (II-i), (II-j), (II-k), (II-l), (II-m), (II-n), (II-o), (II-p), (II-q), or (II-r), or a pharmaceutically acceptable salt, biologically active metabolite, solvate, hydrate, ester, prodrug, enantiomer or stereoisomer thereof.

In certain embodiments of the method of treating micropenis, the compound is of Formula (III). In some embodiments of the method of treating micropenis, the compound is of Formula (IV).

In some embodiments, the method for treating micropenis reduces side effects associated with the administration of non-isotopically enriched testosterone or methyltestosterone.

In some embodiments, a method is provided for treating vulvar dystrophy in a subject in need thereof, the method comprising administering to the subject a pharmaceutical composition comprising an effective amount of a compound of a formula disclosed herein, or a pharmaceutically acceptable salt, biologically active metabolite, solvate, hydrate, ester, prodrug, enantiomer or stereoisomer thereof.

In certain embodiments of the method of treating vulvar dystrophy, the compound is of Formula (I). In certain embodiments, the compound is of Formula (I-A). In certain embodiments, the compound is of Formula (I-B). In certain embodiments, the compound is of Formula (I-C). In certain embodiments, the compound is of Formula (I-D). In certain embodiments, the compound is of Formula (I-E). In certain embodiments, the compound is of Formula (I-F). In certain embodiments, the compound is of Formula (I-G). In certain embodiments, the compound is of Formula (I-H). In certain embodiments, the compound is of Formula (I-I). In certain embodiments, the compound is of Formula (I-J). In certain embodiments, the compound is of Formula (I-K). In certain embodiments, the compound is of Formula (I-L). In certain embodiments, the compound is of Formula (I-M). In certain embodiments, the compound is of Formula (I-N).

In certain embodiments of the method of treating vulvar dystrophy, the compound is Formula (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), (I-s), (I-t), (I-u), or a pharmaceutically acceptable salt, biologically active metabolite, solvate, hydrate, ester, prodrug, enantiomer or stereoisomer thereof.

In certain embodiments of the method of treating vulvar dystrophy, the compound is of Formula (II). In certain embodiments, the compound is of Formula (II-A). In certain embodiments, the compound is of Formula (II-B). In certain embodiments, the compound is of Formula (II-C). In certain embodiments, the compound is of Formula (II-D). In certain embodiments, the compound is of Formula (II-E). In certain embodiments, the compound is of Formula (II-F). In certain embodiments, the compound is of Formula (II-G). In certain embodiments, the compound is of Formula (II-H). In certain embodiments, the compound is of Formula (II-I). In certain embodiments, the compound is of Formula (II-J). In certain embodiments, the compound is of Formula (II-K).

In certain embodiments of the method of treating vulvar dystrophy, the compound is Formula (II-a), (II-b), (II-c), (II-d), (II-e), (II-f), (II-g), (II-h), (II-i), (II-j), (II-k), (II-l), (II-m), (II-n), (II-o), (II-p), (II-q), or (II-r), or a pharmaceutically acceptable salt, biologically active metabolite, solvate, hydrate, ester, prodrug, enantiomer or stereoisomer thereof.

In certain embodiments of the method of treating vulvar dystrophy, the compound is of Formula (III). In some embodiments of the method of treating vulvar dystrophy, the compound is of Formula (IV).

In some embodiments, the method for treating vulvar dystrophy reduces side effects associated with the administration of non-isotopically enriched testosterone or methyltestosterone.

In some embodiments, a method is provided for treating or preventing breast cancer in a subject in need thereof, the method comprising administering to the subject a pharmaceutical composition comprising an effective amount of a compound of a formula disclosed herein, or a pharmaceutically acceptable salt, biologically active metabolite, solvate, hydrate, ester, prodrug, enantiomer or stereoisomer thereof. In certain embodiments, the breast cancer is an advancing inoperable metastatic (skeletal) mammary cancer. In some embodiments, the breast cancer is an advancing inoperable metastatic (skeletal) mammary cancer, and the subject is a female human who is one to five years postmenopausal. In some embodiments, the breast cancer is ductal carcinoma, invasive ductal carcinoma (e.g., tubular carcinoma of the breast, medullary carcinoma of the breast, papillary carcinoma of the breast, cribriform carcinoma of the breast), invasive lobular carcinoma, inflammatory breast cancer, male breast cancer, Paget's disease of the nipple, phyllodes tumors of the breast, or metastatic breast cancer. In some embodiments, the breast cancer is an estrogen receptor positive breast cancer. In some embodiments, the breast cancer is resistant to an aromatase inhibitor, selective estrogen receptor modulator, selective estrogen receptor degrader, or selective androgen receptor modulator. In some embodiments, the breast cancer is an estrogen receptor positive breast cancer and has developed resistance to an aromatase inhibitor therapy.

In certain embodiments of the method of treating or preventing breast cancer, the compound is of Formula (I). In certain embodiments, the compound is of Formula (I-A). In certain embodiments, the compound is of Formula (I-B). In certain embodiments, the compound is of Formula (I-C). In certain embodiments, the compound is of Formula (I-D). In certain embodiments, the compound is of Formula (I-E). In certain embodiments, the compound is of Formula (I-F). In certain embodiments, the compound is of Formula (I-G). In certain embodiments, the compound is of Formula (I-H). In certain embodiments, the compound is of Formula (I-I). In certain embodiments, the compound is of Formula (I-J). In certain embodiments, the compound is of Formula (I-K). In certain embodiments, the compound is of Formula (I-L). In certain embodiments, the compound is of Formula (I-M). In certain embodiments, the compound is of Formula (I-N).

In certain embodiments of the method of treating or preventing breast cancer, the compound is Formula (I-a), (I-b), (I-c), (I-d), (I-e), (I-f), (I-g), (I-h), (I-i), (I-j), (I-k), (I-l), (I-m), (I-n), (I-o), (I-p), (I-q), (I-r), (I-s), (I-t), (I-u), or a pharmaceutically acceptable salt, biologically active metabolite, solvate, hydrate, ester, prodrug, enantiomer or stereoisomer thereof.

In certain embodiments of the method of treating or preventing breast cancer, the compound is of Formula (II). In certain embodiments, the compound is of Formula (II-A). In certain embodiments, the compound is of Formula (II-B). In certain embodiments, the compound is of Formula (II-C). In certain embodiments, the compound is of Formula (II-D). In certain embodiments, the compound is of Formula (II-E). In certain embodiments, the compound is of Formula (II-F). In certain embodiments, the compound is of Formula (II-G). In certain embodiments, the compound is of Formula (II-H). In certain embodiments, the compound is of Formula (II-I). In certain embodiments, the compound is of Formula (II-J). In certain embodiments, the compound is of Formula (II-K).

In certain embodiments of the method of treating or preventing breast cancer, the compound is Formula (II-a), (II-b), (II-c), (II-d), (II-e), (II-f), (II-g), (II-h), (II-i), (II-j), (II-k), (II-l), (II-m), (II-n), (II-o), (II-p), (II-q), or (II-r), or a pharmaceutically acceptable salt, biologically active metabolite, solvate, hydrate, ester, prodrug, enantiomer or stereoisomer thereof.

In certain embodiments of the method of treating breast cancer, the compound is of Formula (III). In some embodiments of the method of treating breast cancer, the compound is of Formula (IV).

In some embodiments, the method for treating or preventing breast cancer reduces side effects associated with the administration of non-isotopically enriched testosterone or methyltestosterone.

In some embodiments, a method is provided for treating or preventing a sexual disorder in a subject in need thereof, the method comprising administering to the subject a pharmaceutical composition comprising an effective amount of a compound of a formula disclosed herein, or a pharmaceutically acceptable salt, biologically active metabolite, solvate, hydrate, ester, prodrug, enantiomer or stereoisomer thereof. Examples of sexual disorders include, but are not limited to, sexual desire disorders such as Hypoactive Sexual Desire Disorder (HSDD) and Sexual Aversion Disorder; sexual arousal disorders such as Female Sexual Arousal Disorder and Male Erectile Disorder; orgasmic disorders such as Female Orgasmic Disorder, Male Orgasmic Disorder, and Premature Ejaculation; sexual pain disorders such as Dyspareunia, Vulvar Vestibulitis Syndrome, Vulvar Vestibulitis, Vaginismus, and Noncoital Pain Disorder; female sexual dysfunction; and sexual dysfunction due to a general medical condition, substance-induced sexual dysfunction, sexual dysfunction due to spinal cord injury, and sexual dysfunction not otherwise specified. In some embodiments, the sexual disorder is a sexual desire disorder or a sexual arousal disorder. In some embodiments, the sexual disorder is a sexual desire disorder. In some embodiments, the sexual disorder is a sexual arousal disorder.

In some embodiments, wherein the subject is a male. In some embodiments, the subject is a female.

In certain embodiments of the method of treating or preventing a sexual disorder, the compound is of Formula (I). In certain embodiments, the compound is of Formula (I-A). In certain embodiments, the compound is of Formula (I-B). In certain embodiments, the compound is of Formula (I-C). In certain embodiments, the compound is of Formula (I-D). In certain embodiments, the compound is of Formula (I-E). In certain embodiments, the compound is of Formula (I-F). In certain embodiments, the compound is of Formula (I-G). In certain embodiments, the compound is of Formula (I-H). In certain embodiments, the compound is of Formula (I-I). In certain embodiments, the compound is of Formula (I-J). In certain embodiments, the compound is of Formula (I-K). In certain embodiments, the compound is of Formula (I-L). In certain embodiments, the compound is of Formula (I-M). In certain embodiments, the compound is of Formula (I-N).

In certain embodiments of the method of treating or preventing a sexual disorder, the compound is Formula (I-a), (I-b), (I-c), (I-d), (I-e), (I-f), (I-g), (I-h), (I-l), (I-j), (I-k), (I-l), (I-m), (I-n), (I-o), (I-p), (I-q), (I-r), (I-s), (I-t), (I-u), or a pharmaceutically acceptable salt, biologically active metabolite, solvate, hydrate, ester, prodrug, enantiomer or stereoisomer thereof.

In certain embodiments of the method of treating or preventing a sexual disorder, the compound is of Formula (II). In certain embodiments, the compound is of Formula (II-A). In certain embodiments, the compound is of Formula (II-B). In certain embodiments, the compound is of Formula (II-D). In certain embodiments, the compound is of Formula (II-E). In certain embodiments, the compound is of Formula (II-F). In certain embodiments, the compound is of Formula (II-G). In certain embodiments, the compound is of Formula (II-H). In certain embodiments, the compound is of Formula (II-I). In certain embodiments, the compound is of Formula (II-J). In certain embodiments, the compound is of Formula (II-K).

In certain embodiments of the method of treating or preventing a sexual disorder, the compound is Formula (II-a), (II-b), (II-c), (II-d), (II-e), (II-f), (II-g), (II-h), (II-I), (II-j), (II-k), (II-l), (II-m), (II-n), (II-o), (II-p), (II-q), or (II-r), or a pharmaceutically acceptable salt, biologically active metabolite, solvate, hydrate, ester, prodrug, enantiomer or stereoisomer thereof.

In certain embodiments of the method of treating a sexual disorder, the compound is of Formula (III). In some embodiments of the method of treating a sexual disorder, the compound is of Formula (IV).

In some embodiments, the method for treating or preventing a sexual disorder reduces side effects associated with the administration of non-isotopically enriched testosterone or methyltestosterone.

In certain embodiments, the methods disclosed herein further comprise administering to the subject in need thereof an additional therapy. In certain embodiments, the additional therapy is an additional pharmaceutical agent. The pharmaceutical compositions of the present disclosure and the additional therapy may show synergy in the methods and uses of the present disclosure. In certain embodiments, the additional pharmaceutical agent is an aromatase inhibitor. In certain embodiments, the additional pharmaceutical agent is a selective estrogen receptor modulator. In certain embodiments, the additional pharmaceutical agent is a selective estrogen receptor degrader. In certain embodiments, the additional pharmaceutical agent is a selective androgen receptor modulator.

In certain embodiments, the methods described herein achieve a lower level of formation of estradiol when compared to the administration the same or equivalent amount of a non-isotopically enriched compound of the same formula. In some embodiments, the methods described herein achieve a lower level of formation of estradiol when compared to the administration the same or equivalent amount of a non-isotopically enriched compound of the same formula when administered by the same route of administration. In certain embodiments, the methods described herein achieve a lower level of formation of estradiol by at least 0.5%, 1%, 2%, 3%, 4%, 5%, 6%, 7%, 8%, 9%, 10%, 15%, 25%, 30%, 35%, 40%, 45%, 50%, 55%, 60%, 65%, 70%, or 75% when compared to the administration of the same or equivalent amount of a non-isotopically enriched compound of the same formula.

In certain embodiments, the methods described herein achieve a higher level of formation of DHT when compared to the administration the same or equivalent amount of a non-isotopically enriched compound of the same formula. In some embodiments, the methods described herein achieve a higher level of formation of DHT when compared to the administration the same or equivalent amount of a non-isotopically enriched compound of the same formula when administered by the same route of administration. In certain embodiments, the methods described herein achieve a higher level of formation of DHT by at least 0.5%, 1%, 2%, 3%, 4%, 5%, 6%, 7%, 8%, 9%, 10%, 15%, 25%, 30%, 35%, 40%, 45%, 50%, 55%, 60%, 65%, 70%, or 75% when compared to the administration of the same or equivalent amount of a non-isotopically enriched compound of the same formula.

The amount of testosterone, estradiol or DHT present in a subject before and after administration of a compound or pharmaceutical composition described herein may be determined by measuring the presence of those hormones in blood samples. In some embodiments, estradiol is measured in blood samples taken at 0, 15, 30, or 45 minutes; or 1, 2, 3, 4, 5, 6, 9, 12, 24, 27, 30, 33, 36, 48, 54, 60, 72, 78, or 84 hours after dosing. In some embodiments, DHT is measured in blood samples taken at 0, 15, 30, or 45 minutes; or 1, 2, 3, 4, 5, 6, 9, 12, 24, 27, 30, 33, 36, 48, 54, 60, 72, 78, or 84 hours after dosing.

In certain embodiments, the methods described herein result in a blood plasma half-life ($t_{1/2}$) of the administered compound that is longer than that of the same or equivalent amount of a non-isotopically enriched compound having the same formula when administered by the same route of administration. In some embodiments, the blood plasma half-life ($t_{1/2}$) of the compound is at least 5%, 10%, 25%, 50%, 100%, 200%, 300%, 400%, or 500% longer than the same or equivalent amount of a non-isotopically enriched compound having the same formula when administered by the same route of administration.

In certain embodiments, the methods described herein result in a time of maximum plasma concentration ($T_{max}$) of the administered compound that is longer than that of the same or equivalent amount of a non-isotopically enriched compound having the same formula when administered by the same route of administration. In some embodiments, the time of maximum plasma concentration ($T_{max}$) of the compound is at least 5%, 10%, 25%, 50%, 100%, 200%, 300%, or 400% longer than that of the same or equivalent amount of a non-isotopically enriched compound having the same formula when administered by the same route of administration.

In certain embodiments, the methods described herein result in a maximum plasma concentration ($C_{max}$) of the administered compound that is substantially similar to that of the same or equivalent amount of a non-isotopically enriched compound having the same formula when administered by the same route of administration.

In some embodiments, the maximum plasma concentration ($C_{max}$) of the administered compound is lower than that of the same or equivalent amount of a non-isotopically enriched compound having the same formula when administered by the same route of administration. In certain embodiments, the maximum plasma concentration ($C_{max}$) of the administered compound is at least 5%, 10%, 25%, or 50% lower than that of the same or equivalent amount of a non-isotopically enriched compound having the same formula when administered by the same route of administration.

In some embodiments of the methods described herein, the total systemic exposure (AUC) in plasma of the administered compound is greater than that of the same or equivalent amount of a non-isotopically enriched compound having the same formula when administered by the same route of administration. In certain embodiments, the total systemic exposure (AUC) in plasma is at least 5%, 10%, 25%, 50%, 100%, or 200% greater than that of the same or equivalent amount of a non-isotopically enriched compound having the same formula when administered by the same route of administration.

In certain embodiments, the methods described herein avoid or reduce the incidence of one or more side effects or adverse reactions associated with non-isotopically enriched testosterone, methyltestosterone, or derivatives thereof, at an equivalent dose. In some embodiments, the side effect is hypertension (increase in blood pressure), increase in heart rate, polycythemia, a major adverse cardiovascular event (e.g., myocardial infarction, stroke, and cardiovascular death), worsening of benign prostatic hyperplasia (BPH), prostate cancer, a venous thromboembolic event (e.g., deep vein thrombosis (DVT) and pulmonary embolism (PE)), adverse effects on spermatogenesis, hepatic adverse events (e.g., peliosis hepatis, hepatic neoplasms, cholestatic hepatitis, and jaundice, including hepatic adenoma with long term use), edema, gynecomastia, breast cancer, breast pain, sleep apnea, a change in serum lipid profile, hypercalcemia, decreased concentration of thyroxin-binding globulin, depression, suicidal ideation, diarrhea, dyspepsia, eructation, peripheral edema, nausea, increased hematocrit, headache, prostatomegaly, or acne. In certain embodiments, the side effect is hypertension, increase in heart rate, polycythemia, a major adverse cardiovascular events, worsening of benign prostatic hyperplasia, prostate cancer, a venous thromboembolic event, an adverse effect on spermatogenesis, a hepatic adverse event, edema, gynecomastia, breast cancer, breast pain, sleep apnea, a change in serum lipid profile, hypercalcemia, decreased concentration of thyroxin-binding globulin, depression, suicidal ideation, diarrhea, dyspepsia, eructation, peripheral edema, nausea, increased hematocrit, headache, or prostatomegaly.

In some embodiments, the administration of a compound of Formula (I), (II), (III), or (IV), or a pharmaceutically acceptable salt, biologically active metabolite, solvate, hydrate, ester, prodrug, enantiomer or stereoisomer thereof, results in an increased duration of action, reduction in frequency of administration, increase in patient compliance and/or ease of use relative to the administration of testosterone or a testosterone derivative (i.e., non-deuterated testosterone or derivative) at an equivalent dose. In some embodiments, the composition comprising a compound of Formula (I), (II), (III), or (IV), or a pharmaceutically acceptable salt, biologically active metabolite, solvate, hydrate, ester, prodrug, enantiomer or stereoisomer thereof, is administered at a lower dose strength, lower daily dose, more frequent or less frequent daily dosing intervals, and/or for a shorter total period of administration than a non-isotopically enriched testosterone or testosterone derivative.

In some embodiments, the administration of a compound of Formula (I), (II), (III), or (IV), or a pharmaceutically acceptable salt, biologically active metabolite, solvate, hydrate, ester, prodrug, enantiomer or stereoisomer thereof, reduces the need for the co-administration of an aromatase inhibitor, a selective estrogen receptor modulator (SERM), or selective estrogen receptor degrader (SERD). In some embodiments, the composition comprising a compound of Formula (I), (II), (III), or (IV), or a pharmaceutically acceptable salt, biologically active metabolite, solvate, hydrate, ester, prodrug, enantiomer or stereoisomer thereof, may be safely and effectively administered to a subject in need thereof without the co-administration of an aromatase inhibitor or SERM.

In another aspect, provided herein is a method of determining the effect of a compound provided herein (e.g., a compound of Formula (I), (II), (III), or (IV), or a pharmaceutically acceptable salt, biologically active metabolite, solvate, hydrate, ester, prodrug, enantiomer or stereoisomer thereof) following administration of the compound to a subject in need thereof, comprising administering the compound to the subject, and detecting the level, or change in the level, of endogenous testosterone, or one or more metabolites thereof, or of the compound, or one or more metabolites thereof, in the subject. In certain embodiments, the method further comprises determining the optimal dosage, timing, or formulation for a subsequent administration of the compound or composition, and, optionally, administering a subsequent dose of the compound or composition to the subject.

In some embodiments, the method comprises determining or detecting the level of endogenous testosterone, or a derivative of endogenous testosterone such as estradiol or 5α-dihydrotestosterone (DHT), prior to administration of compound (e.g., a compound of Formula (I), (II), (III), or (IV)) to a subject. In some embodiments, the level may be determined or detected in blood plasma. In some embodiments, the method comprises obtaining blood samples at predetermined time point (e.g., every 15, 30, 45 minutes, or every 1 h, 2 h, 4 h, 6 h, 12 h), or at specific time of day (e.g., starting at 0800 h), or a combination of both (e.g., every 30 minutes starting at 0800 h for a period of 14 h).

In some embodiments, the method comprises determining or detecting the level, or change in the level, of endogenous testosterone following administration of a compound provided herein (e.g., a compound of Formula (I), (II), (III), or (IV)). In some embodiments, the method comprises determining or detecting the level, or change in the level, of an administered compound (e.g., a compound of Formula (I), (II), (III), or (IV)). In some embodiments, the method comprises determining or detecting the level, or change in the level, of both endogenous testosterone and an administered compound of Formula (I), (II), (III), or (IV). In some embodiments, the method comprises comparing the level of endogenous testosterone prior to and following administration of a compound provided herein to determine the effect of the compound on the level of endogenous testosterone.

In some embodiments, the method comprises determining or detecting the level, or change in the level, of one or more metabolites of endogenous testosterone. In some embodiments, the metabolite is estradiol. In some embodiments, the metabolite is 5α-dihydrotestosterone (DHT). In some embodiments, the method comprises determining or detecting the level, or change in the level, of metabolites of a compound of Formula (I), (II), (III), or (IV). In some embodiments, the metabolite is a deuterated form of estradiol. In some embodiments, the metabolite is a deuterated form of 5α-dihydrotestosterone (DHT). In some embodiments, the method comprises determining or detecting the level, or change in the level, of metabolites of both endogenous testosterone and of a compound of Formula (I), (II), (III), or (IV). In some embodiments, the method comprises comparing the level of the metabolite prior to and following administration of a compound provided herein to determine the effect of the compound on the level of the metabolite.

In some embodiments, the method comprises determining or detecting the level, or change in the level, of the amount or concentration of a compound provided herein, or one or more metabolites thereof. In some embodiments, determining or detecting the level, or change in the level, of the compound, or one or more metabolites thereof, comprises measuring one or more pharmacokinetic parameters. In some embodiments, the pharmacokinetic parameters are determined or detected by obtaining blood plasma samples from the subject. In some embodiments, the blood plasma samples are taken prior to and after administration of the compound at specified time points (e.g., 5 min before and 0.25, 0.5, 0.75, 1, 1.25, 1.5, 1.75, 2, 2.5, 3, 3.5, 4, 6, 8, 10, 12, 14, 24, 48, 72, or 96 h or more after dosing). In some embodiments, the method comprises measuring the half-life ($t_{1/2}$) of a compound provided herein, or one or more metabolites thereof. In some embodiments, the method comprises measuring the total systemic exposure (AUC) of a compound provided herein, or one or more metabolites thereof. In some embodiments, the method comprises measuring the maximum plasma concentration ($C_{max}$) of a compound provided herein, or one or more metabolites thereof. In some embodiments, the method comprises measuring time of maximum plasma concentration ($T_{max}$) of a compound provided herein, or one or more metabolites thereof. In some embodiments, the method comprises measuring the blood plasma concentration at each of the specified time points.

In some embodiments, the detecting is performed by mass spectrometry. In some embodiments, the detecting is performed by a separation technique coupled to mass spectrometry. In some embodiments, the detecting is performed by chromatography coupled to mass spectrometry. In some embodiments, the detecting is performed by gas chromatography mass spectrometry (GC-MS). In some embodiments, the detecting is performed by liquid chromatography mass spectrometry (LC-MS). In some embodiments, the detecting is performed by high-pressure liquid chromatography mass spectrometry (HPLC-MS).

In some embodiments, the detecting is performed using one or more internal standards. In some embodiments, the internal standard comprises one or more isotopic labels (e.g., deuterium, $^{13}C$, $^{15}N$, or $^{18}O$). In some embodiments, the internal standard comprises multiple instances of the same isotopic label. In some embodiments, the internal standard comprises multiple different isotopic labels (e.g., $^{13}C$ and deuterium). In some embodiments, the internal standard is introduced prior to chromatographic separation. In some embodiments, the compound provided herein and the internal standard have distinct isotope content.

In some embodiments, the method further comprises determining the optimal dosage for a subsequent administration of the compound and, optionally, administering a subsequent dose of the compound to the subject. In certain embodiments, the optimal dosage is the same as a previous dosage. In some embodiments, the optimal dosage is greater than a previous dosage. In certain embodiments, the optimal dosage is less than a previous dosage.

In some embodiments, the method further comprises determining the optimal timing for a subsequent administration of the compound and, optionally, administering a subsequent dose of the compound to the subject. In certain embodiments, the optimal timing comprises more frequent administration. In some embodiments, the optimal timing comprises less frequent administration. In certain embodiments, the optimal timing comprises administration with the same frequency.

In certain embodiments, the method further comprises determining the optimal formulation for a subsequent administration of the compound and, optionally, administering a subsequent dose of the compound to the subject. In some embodiments, the optimal formulation is for a different route of administration. In certain embodiments, the optimal formulation is for the same route of administration. In some embodiments, the optimal formulation is the same formulation. In certain embodiments, the optimal formulation is a different formulation. In some embodiments, the optimal formulation comprises a higher effective amount of a compound provided herein, or a pharmaceutically acceptable salt, biologically active metabolite, solvate, hydrate, ester, prodrug, enantiomer or stereoisomer thereof. In certain embodiments, the optimal formulation comprises the same effective amount of a compound provided herein, or a pharmaceutically acceptable salt, biologically active metabolite, solvate, hydrate, ester, prodrug, enantiomer or stereoisomer thereof. In some embodiments, the optimal formulation comprises a lower effective amount of a compound provided herein, or a pharmaceutically acceptable salt, biologically active metabolite, solvate, hydrate, ester, prodrug, enantiomer or stereoisomer thereof. In some embodiments, the optimal formulation comprises a different pharmaceutically acceptable salt, biologically active metabolite, solvate, hydrate, ester, prodrug, enantiomer or stereoisomer of a compound provided herein. In some embodiments, the optimal formulation comprises a different compound provided herein, or a pharmaceutically acceptable salt, biologically active metabolite, solvate, hydrate, ester, prodrug, enantiomer or stereoisomer thereof.

In some embodiments, the optimal formulation comprises an additional pharmaceutical agent. In some embodiments, the additional pharmaceutical agent is a selective estrogen receptor modulator (SERM) or selective estrogen receptor degrader (SERD). In some embodiments, the additional pharmaceutical agent is an aromatase inhibitor. In some embodiments, the additional pharmaceutical agent is an anti-proliferative agent. In certain embodiments, the additional pharmaceutical agent is an anti-cancer agent. In certain embodiments, the additional pharmaceutical agent is a hormone receptor modulator or degrader (e.g., estrogen receptor modulators and androgen receptor modulators).

The representative examples, which follow, are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that, unless otherwise indicated, the entire contents of each of the references cited herein are incorporated herein by reference to help illustrate the state of the art. The following examples contain important additional information, exemplification and guidance, which can be adapted to the practice of this invention in its various embodiments and the equivalents thereof.

These and other aspects of the present invention will be further appreciated upon consideration of the following Examples, which are intended to illustrate certain particular embodiments of the invention but are not intended to limit its scope, as defined by the claims.

EXAMPLES

In order that the disclosure described herein may be more fully understood, the following examples are set forth. The synthetic and biological examples described in this application are offered to illustrate the compounds, compositions, food products, beverages, and methods provided herein and are not to be construed in any way as limiting their scope.

ABBREVIATIONS

Ag. Agonist
Ant. Antagonist
FWHM Full width at half maximum
MS Mass spectrometry
min Minute(s)
ND Not determined
$t_{1/2}$ Terminal half-life UPLC Ultra performance liquid chromatography Deuterated testosterone, i.e., a compound of Formula (I) as described herein, may be prepared as described in Baba et al., "Synthesis of trideuterated testosterone labeled selectively at the C-19 angular methyl group," *J Label Compd Radiopharm*, 14: 783-791 (1978); Stefan A. Wudy, "Synthetic procedures for the preparation of deuterium-labeled analogs of naturally occurring steroids," Steroids, 55, 10, 463-471 (1990); and Dehennin et al., "Simple methods for the synthesis of twenty different, highly enriched deuterium labelled steroids, suitable as internal standards for isotope dilution mass spectrometry," Biomed. Mass Spectrom., 7:493-499 (1980), the disclosures of which are incorporated herein by reference in their entirety.

Deuterated forms of compounds of Formula (II) may be prepared, for example, as described in Baba et al., "Synthesis of deuterium labeled 17-methyl-testosterone," *Steroids*, 44(3):253-60 (1984), and El-Desoky et al., "Synthesis and chemical reactions of the steroidal hormone 17α-methyltestosterone," 105: 68-95 (2016), the disclosures of which are incorporated herein by reference in their entirety.

Enol ethers of testosterone and methyltestosterone may be prepared as described in Ercoli et al., "An Improved Method of Preparing Testosterone, Dihydrotestosterone and Some of their Esters," *J Am Chem Soc*, 75:650-653 (1953), U.S. Pat. Nos. 3,053,735A, 2,363,338A, 3,019,241A, and 2,835, 667A. R" can be varied by substituting the appropriate alcohol (HO—R"). Deuterated forms of compounds of Formula (IV) may be prepared, for example, as described in El-Desoky et al., "Synthesis and chemical reactions of the steroidal hormone 17α-methyltestosterone," 105: 68-95 (2016), the disclosure of which is incorporated herein by reference in its entirety.

Example 1

A study was performed to determine the metabolic stability of testosterone and testosterone-19-d3 in the presence of recombinant CYP19 (aromatase).

The incubation conditions used are described in Table 1.
Table 1. Incubation Conditions
Sample type: Recombinant CYP19 (Human, Supersome/ Corning lot 456266/5254002)
Incubation volume: 300 μl, 0.1 M phosphate buffer pH 7.4+2 mM MgCl2
Concentration and protein content A: 0.5 μM; 4 pmol/ml
Concentration and protein content B: 2 μM; 10 pmol/ml
Cofactors & concentrations: NADPH (1 mM)
Incubation times: 0, 10, 20, 40 and 60 min @ 37° C.
Replicates: 2 with cofactors, 1 without cofactors
Reaction started by: Addition of study compound
Termination of incubations: 2-fold volume of cold 75% acetonitrile
Sampling volume: 40 μL
Storage of the samples: Immediate analysis after sample preparation
The analytical method used is described in Table 2.
Table 2. Analytical Method
Instrumentation: Waters Aquity UPLC+Thermo Q-Exactive Focus Orbitrap MS
Column: Waters BEHC18 (2.1×50 mm, 1.7 μm particle size)
Gradient Elution; A=0.1% formic acid, B=acetonitrile

| Time (min) | Flow | A % | B % | curve |
|---|---|---|---|---|
| 0 | 0.500 mL/min | 98 | 2 | — |
| 0.5 | 0.500 mL/min | 98 | 2 | 6 |
| 4 | 0.500 mL/min | 50 | 50 | 6 |
| 4.5 | 0.500 mL/min | 2 | 95 | 6 |
| 5 | 0.500 mL/min | 2 | 95 | 6 |
| 6 | 0.500 mL/min | 98 | 2 | 1 |

Temperature: 40 (° C.)

Injection Volume: 4 (μL)

Ionization polarity: ESI+

Sheath gas: nitrogen 50 units

Auxiliary gas: nitrogen 10 units

Sweep gas: nitrogen 3 units

Capillary voltage: 3000 V

Capillary temperature: 320 (° C.)

Auxiliary gas heater temperature: 500 (° C.)

Mass range: m/z 70-1000

Acquisition time: 7 Hz for full scan, IT 100 ms for DDI MS/MS

Resolution: 35 000 (FWHM @ m/z 200) for full scan, 17 500 for MS/MS in DDI mode

Normalized collision energy: off for full scan; 20+40+60 for DDI MS/MS (inclusion list for expected metabolites ON; also other unexpected most abundant metabolites chosen for MS/MS)

Calibration: External

Software: Thermo Xcalibur 4.1.31.9

Ion chromatogram window: 5 ppm

Figure 1B:
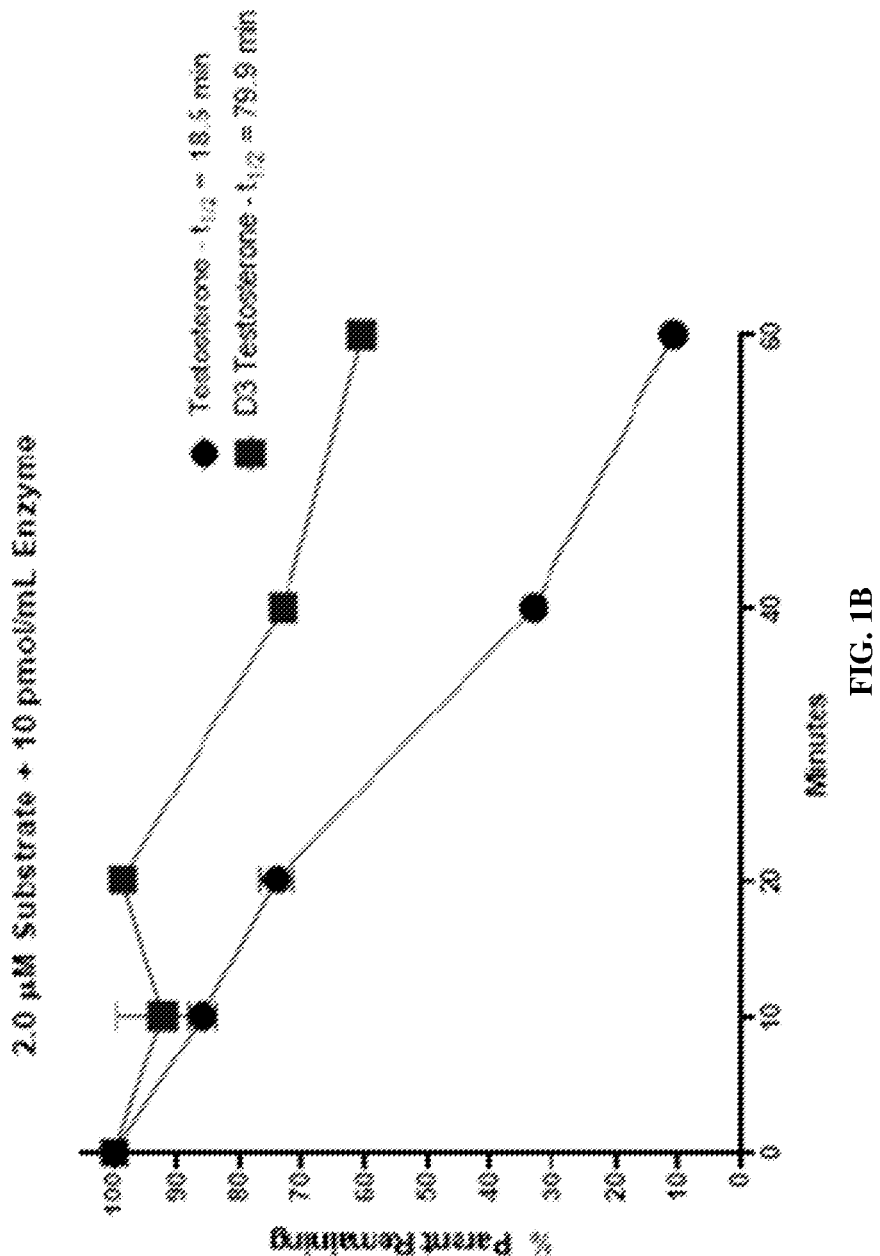
Figure 2:
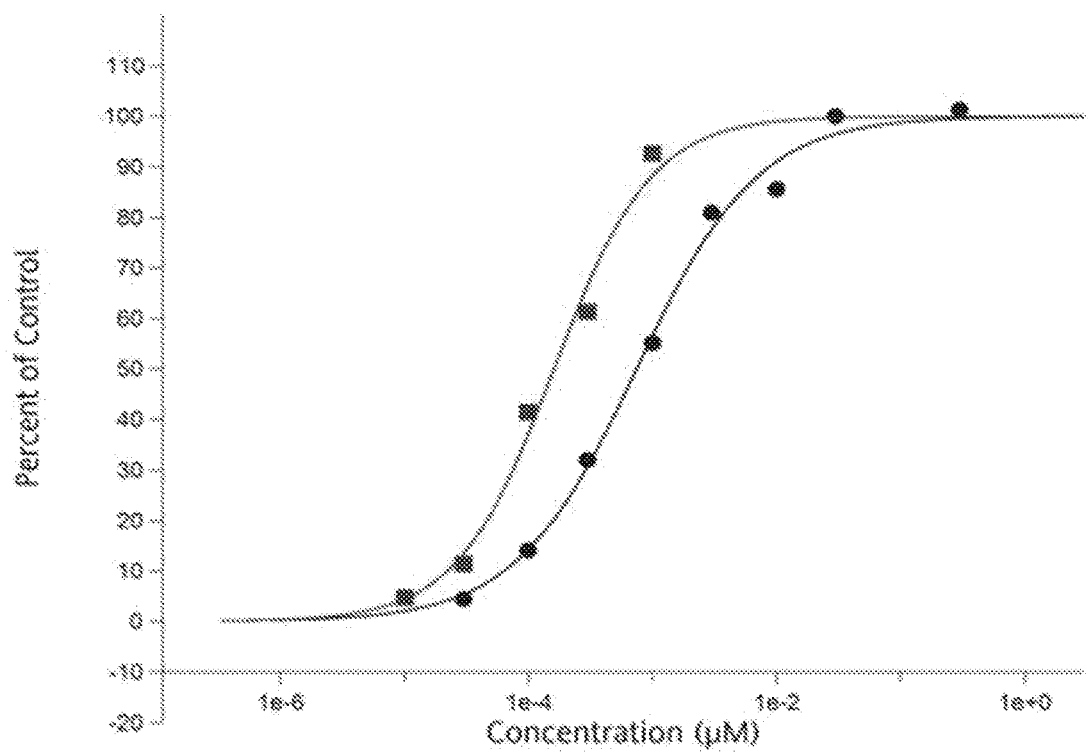
FIG. 2 shows the response curve of testosterone relative to that of 5α-dihydrotestosterone for androgen receptor translocation in human CHO-K1 cells.
Figure 3:
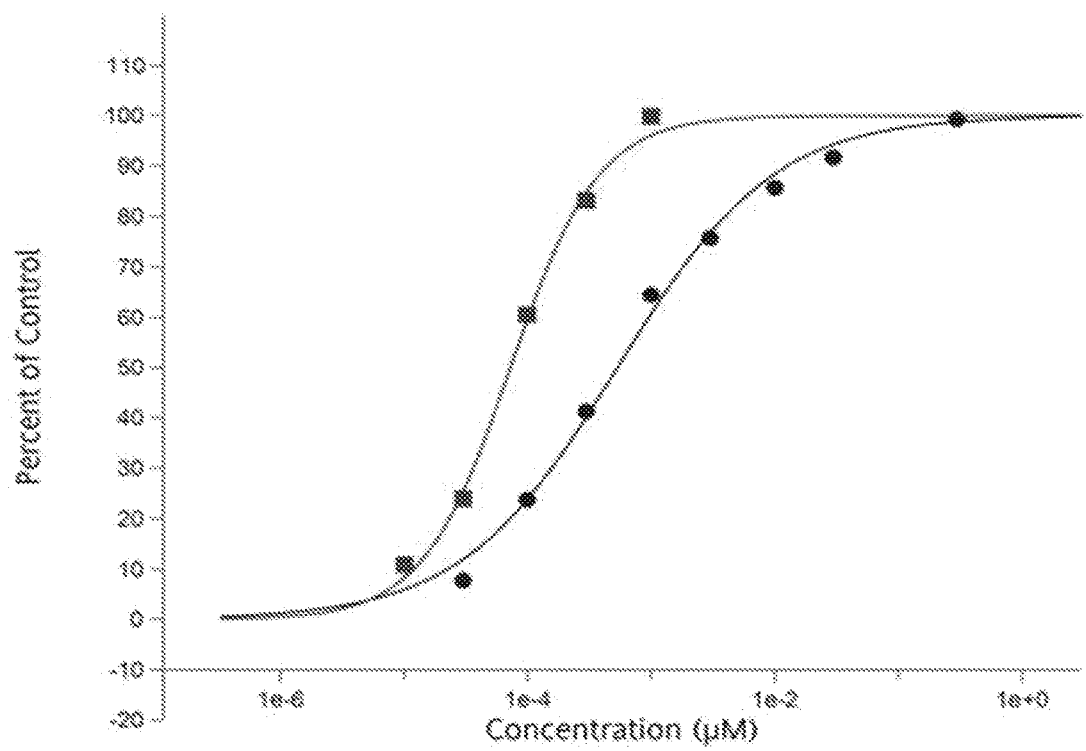
FIG. 3 shows the response curve of testosterone-19-d3 relative to that of 5α-dihydrotestosterone for androgen receptor translocation in human CHO-K1 cells.

The results of the study are shown in FIG. 1. The study demonstrated an unexpected and significant difference in the metabolic stability of testosterone and testosterone-19-d3 in the presence of recombinant CYP19 (aromatase). Specifically, the study demonstrated that testosterone-19-d3 had substantially higher stability than testosterone in the presence of aromatase, and was more resistant to clearance by aromatase. The half-life ($t_{1/2}$) of testosterone-19-d3 in aromatase was between 4-7 times longer than that of non-isotopically enriched testosterone.

Example 2

A study was performed to evaluate the activity of testosterone or testosterone-19-d3 for androgen receptor translocation in human CHO-K1 cells. Results are summarized in Tables 1 and 2. Target: human CHO-K1 cells Chinese hamster ovary. Vehicle: 0.1% DMSO. Incubation Time/ Temp.: 8 hours at 37° C. Incubation buffer: phenol red-free DMEM/F-12 supplemented with 5% charcoal-stripped FBS. Quantitation Method: High-content Imaging Assay. Signif. Criteria Ag.: ≥50% increase of AR translocation relative to 5α-dihydrotestosterone response. Signif. Criteria Ant.: ≥50% decrease of AR translocation relative to 5α-dihydrotestosterone response. Where presented, $EC_{50}$ values were determined by a non-linear, least squares regression analysis using MathIQ™ (ID Business Solutions Ltd., UK).

TABLE 1

EC$_{50}$ of testosterone or testosterone-19-d3 for androgen receptor translocation.

| Compound | Species | Cell Name | Conc. Criteria | % Response Ag. | % Response Ant. | EC$_{50}$ |
|---|---|---|---|---|---|---|
| Testosterone | human | CHO-K1 | 1 nM ≥ ±50% | 55% | ND | 0.74 nM |
| Testosterone-19-d3 | human | CHO-K1 | 1 nM ≥ ±50% | 64% | ND | 0.53 nM |

TABLE 2

Response data for testosterone or testosterone-19-d3 for androgen receptor translocation.

| Compound | Species | Cell Name | Repetitions | Conc. Criteria | % Response Ag. | % Response Ant. |
|---|---|---|---|---|---|---|
| Testosterone | human | CHO-K1 | 3 | 0.3 μM ≥ ±50% | 101% | ND |
| | | | 3 | 0.03 μM ≥ ±50% | 100% | ND |
| | | | 3 | 10 nM ≥ ±50% | 86% | ND |
| | | | 3 | 3 nM ≥ ±50% | 81% | ND |
| | | | 3 | 1 nM ≥ ±50% | 55% | ND |
| | | | 3 | 0.3 nM ≥ ±50% | 32% | ND |
| | | | 3 | 0.1 nM ≥ ±50% | 14% | ND |
| | | | 3 | 0.03 nM ≥ ±50% | 4% | ND |
| Testosterone-19-d3 | human | CHO-K1 | 3 | 0.3 μM ≥ ±50% | 99% | ND |
| | | | 3 | 0.03 μM ≥ ±50% | 92% | ND |
| | | | 3 | 10 nM ≥ ±50% | 86% | ND |
| | | | 3 | 3 nM ≥ ±50% | 76% | ND |
| | | | 3 | 1 nM ≥ ±50% | 64% | ND |
| | | | 3 | 0.3 nM ≥ ±50% | 41% | ND |
| | | | 3 | 0.1 nM ≥ ±50% | 24% | ND |
| | | | 3 | 0.03 nM ≥ ±50% | 8% | ND |

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising," "including," and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

What is claimed is:

1. A method of treating a sexual disorder in a subject in need thereof, the method comprising administering to the subject a pharmaceutical composition comprising an effective amount of a compound of Formula (I-d):

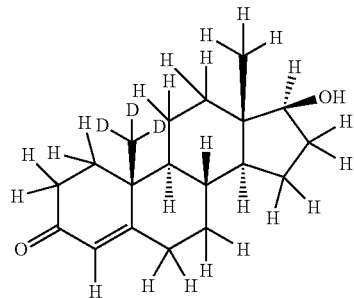

or a pharmaceutically acceptable salt or prodrug thereof, and a pharmaceutically acceptable carrier, wherein the prodrug is selected from the group consisting of the cypionate, enanthate, propionate, and undecanoate prodrugs of the compound of Formula (I-d), and wherein the subject is a female human.

2. The method of claim 1, wherein the composition is administered orally, by injection, transdermally, by implantation, or parenterally.

3. The method of claim 2, wherein the composition is a gel.

4. The method of claim 2, wherein the composition is a transdermal film or patch.

5. The method of claim 2, wherein the composition is a solid dosage formulation.

6. The method of claim 2, wherein the composition is a liquid-filled capsule.

7. The method of claim 1, wherein the sexual disorder is a sexual desire disorder, a sexual aversion disorder, a sexual arousal disorder, an orgasmic disorder, a sexual pain disorder, or sexual dysfunction.

8. The method of claim 7, wherein the sexual disorder is a sexual desire disorder or a sexual arousal disorder.

9. The method of claim 1, wherein the subject is an adult.

10. The method of claim 9, wherein the subject is young adult, middle-aged adult, or senior adult.

11. The method of claim 1, wherein the subject is a premenopausal woman.

12. The method of claim 1, wherein the subject is a postmenopausal woman.

13. The method of claim 1, wherein the administration achieves a total amount of testosterone comparable or equivalent to the physiological testosterone concentration in the subject when premenopausal, or to an average physiological testosterone concentration in a premenopausal female subject.

14. The method of claim 1, wherein the subject is a premenopausal or postmenopausal female, and wherein the method further comprises determining a level of testosterone in the premenopausal or postmenopausal female prior to administering the pharmaceutical composition.

15. The method of claim 1, wherein the method further comprises comparing a level of endogenous testosterone in the subject prior to and following administration of the pharmaceutical composition.

16. The method of claim 1, wherein the method avoids one or more side effects arising from the administration of non-isotopically enriched testosterone.

17. The method of claim 16, wherein the one or more side effects are hypertension, increase in heart rate, polycythemia, a major adverse cardiovascular event, worsening of benign prostatic hyperplasia, prostate cancer, a venous thromboembolic event, a hepatic adverse event, edema, gynecomastia, breast pain, sleep apnea, changes in serum lipid profile, hypercalcemia, decreased concentration of thyroxin-binding globulin, depression, suicidal ideation, diarrhea, dyspepsia, eructation, peripheral edema, nausea, increased hematocrit, or headache.

18. The method of claim 1, wherein the effective amount is between 25 µg and 1,000 mg.

19. The method of claim 1, wherein the method achieves a lower level of formation of estradiol when compared to the administration of an equivalent amount of non-isotopically enriched testosterone.

20. The method of claim 19, wherein the method achieves at least about a 25%, 30%, 35%, 40%, 45%, 50%, 55%, 60%, 65%, 70%, or 75% lower level of formation of estradiol compared to the administration of an equivalent amount of non-isotopically enriched testosterone.

* * * * *